(12) United States Patent
Bettenga

(10) Patent No.: US 11,331,112 B2
(45) Date of Patent: May 17, 2022

(54) ADJUSTABLE DEPTH LIMITING DRILL GUIDE AND SUTURE TRANSPORTING METHOD

(71) Applicant: Mason James Bettenga, Memphis, TN (US)

(72) Inventor: Mason James Bettenga, Memphis, TN (US)

( * ) Notice: Subject to any disclaimer, the term of this patent is extended or adjusted under 35 U.S.C. 154(b) by 77 days.

(21) Appl. No.: 17/090,680

(22) Filed: Nov. 5, 2020

(65) Prior Publication Data

US 2021/0128178 A1 May 6, 2021

Related U.S. Application Data

(60) Provisional application No. 62/931,364, filed on Nov. 6, 2019.

(51) Int. Cl.
*A61B 17/17* (2006.01)

(52) U.S. Cl.
CPC .......... *A61B 17/1796* (2013.01); *A61B 17/17* (2013.01); *A61B 17/1725* (2013.01); *A61B 17/1728* (2013.01)

(58) Field of Classification Search
CPC . A61B 17/1796; A61B 17/17; A61B 17/0482; A61B 17/1725; A61B 17/1728
See application file for complete search history.

(56) References Cited

U.S. PATENT DOCUMENTS

| 6,375,658 | B1 * | 4/2002 | Hangody | ............ | A61F 2/30756 |
|---|---|---|---|---|---|
| | | | | | 623/20.18 |
| 7,575,578 | B2 | 8/2009 | Wetzler | | |
| 7,771,441 | B2 | 8/2010 | Cerundolo | | |
| 8,313,492 | B2 | 11/2012 | Wong | | |
| 8,361,079 | B2 | 1/2013 | Pandya | | |
| 8,491,595 | B2 | 7/2013 | Volpi | | |
| 8,690,885 | B2 | 4/2014 | Smith | | |
| 8,740,913 | B2 | 6/2014 | Schneider | | |
| 8,951,263 | B2 * | 2/2015 | Sinnott | ............... | A61B 17/1739 |
| | | | | | 606/103 |
| 9,662,105 | B2 | 5/2017 | Sinnott | | |
| 10,098,646 | B2 | 10/2018 | Ardito | | |
| 10,123,813 | B2 * | 11/2018 | Boileau | ............... | A61B 17/1796 |
| 10,238,378 | B2 | 3/2019 | Bonutti | | |
| 10,307,173 | B2 | 6/2019 | Ardito | | |
| 2005/0222571 | A1 * | 10/2005 | Ryan | ................... | A61B 17/1617 |
| | | | | | 606/172 |
| 2010/0121337 | A1 | 5/2010 | Pandya | | |
| 2012/0123417 | A1 * | 5/2012 | Smith | ................ | A61B 17/1714 |
| | | | | | 606/98 |
| 2014/0018810 | A1 * | 1/2014 | Knape | ................ | A61B 17/1633 |
| | | | | | 606/80 |

* cited by examiner

*Primary Examiner* — Christian A Sevilla

(57) ABSTRACT

A surgical guide system comprises a guide body having a receiver and a reference plate joined by a connecting arm, a portion of the receiver and a portion of the reference plate intersecting a guide axis, the guide body operable for at least one bone to be interposed between the receiver and reference plate. The guide body further comprising a shuttle cable configured on the reference plate for engagement with a surgical tool A method includes positioning the surgical guide system on at least one bone, the bone the having a first side and a second side, guiding a surgical tool through a hole in the at least one bony structure, engaging a portion of the shuttle cable, and retrieving a first end of the shuttle cable through the hole.

19 Claims, 25 Drawing Sheets

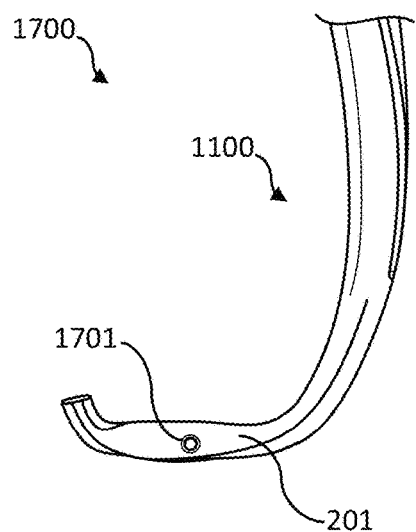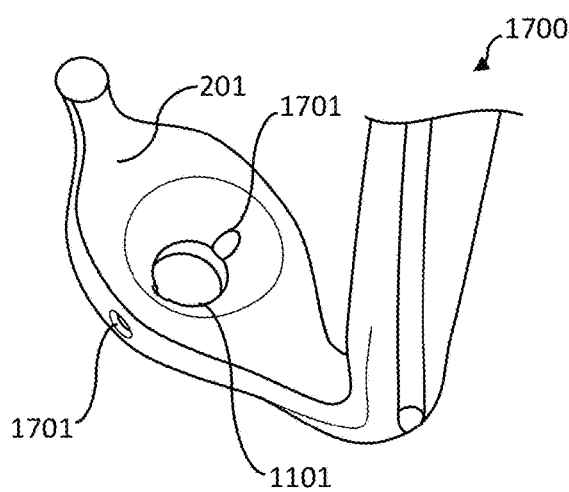
FIG. 17A
FIG. 17B
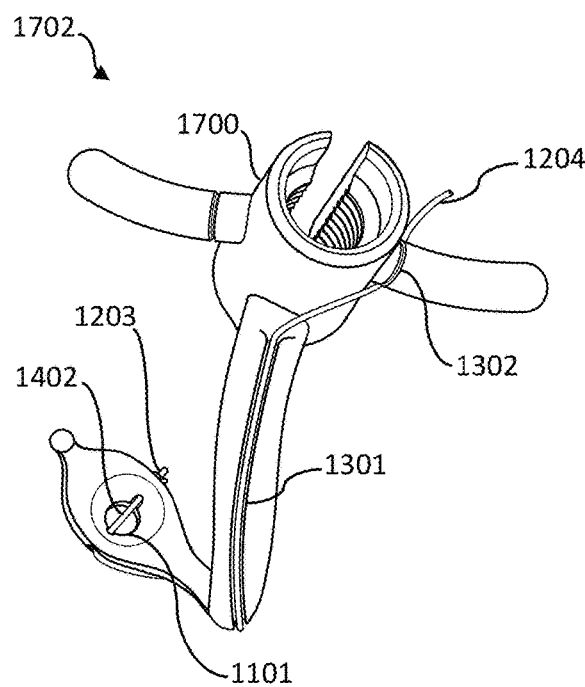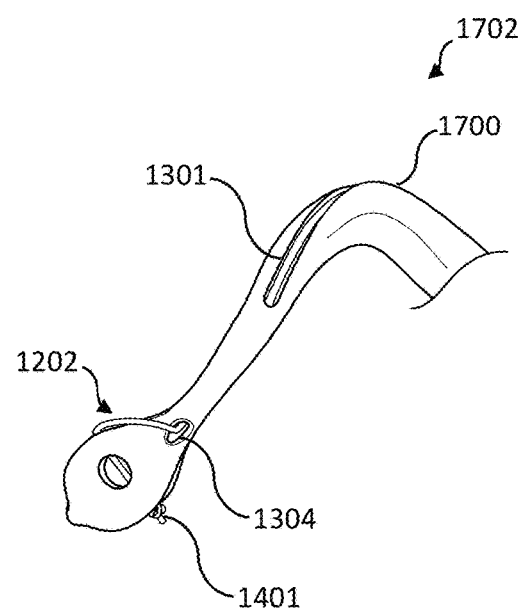
FIG. 17C
FIG. 17D

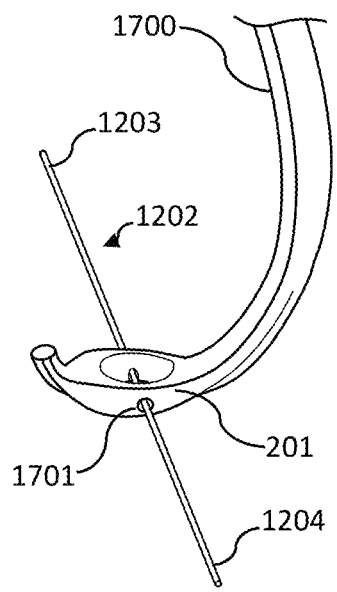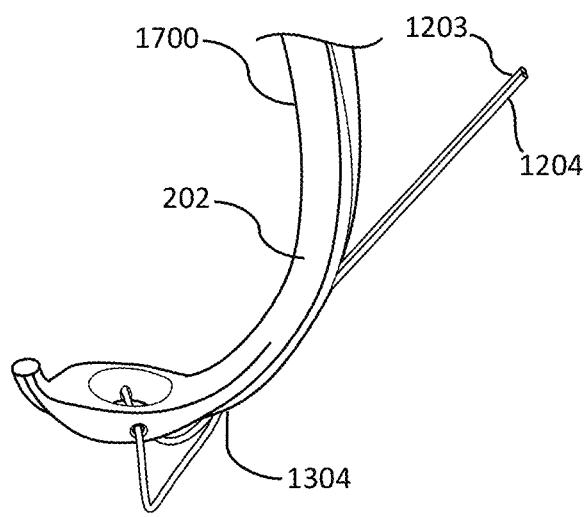
FIG. 18A  FIG. 18B
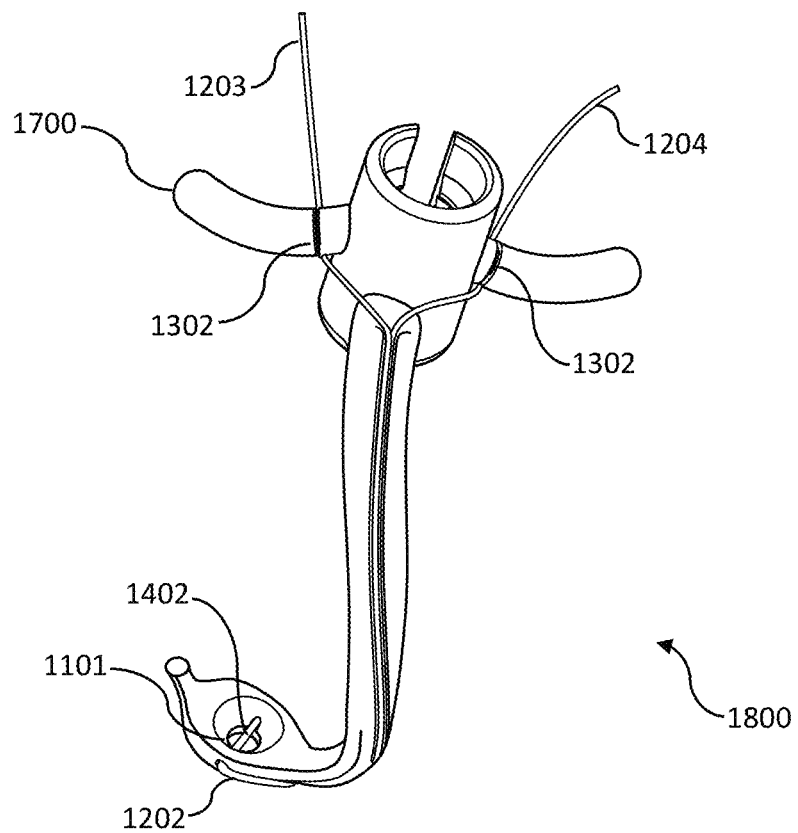
FIG. 18C

ADJUSTABLE DEPTH LIMITING DRILL GUIDE AND SUTURE TRANSPORTING METHOD

CROSS REFERENCE TO RELATED APPLICATIONS

This application claims priority to U.S. Provisional App. No. 62/931,364 filed Nov. 6, 2019, titled ADJUSTABLE DEPTH LIMITING DRILL GUIDE AND SUTURE TRANSPORTING METHOD, herein incorporated by reference in its entirety for all purposes.

FIELD OF THE INVENTION

The present invention relates to devices and methods for orthopedic tissue reconstruction procedures requiring drilling through bone tissue.

BACKGROUND

In the field of orthopedic surgery, several different instruments have been developed for guiding a drill or other surgical instrument along a preferred trajectory though a bone in order to perform a reconstruction of a damaged ligament or reduce a fracture. In some cases, after drilling through tissue, a shuttle cable, commonly a surgical suture or wire, is passed through the drill hole to aid in the transportation of other surgical devices through the hole. One problem encountered with the available adjustable drill guide systems which rely on a solid portion of the drill guide contacting the drill tip to act as the depth limiting feature, is the potential for the cutting portion of the drill tip to be damaged as it contacts the limiting surface, possibly contributing to a foreign material load if it begins to cut into the depth limiting surface.

A limitation of current available drill guides, which include a suture passing capability, is reliance on connecting the shuttle suture to the drill guide through the drill hole, without confirmation of a secure connection, before being removed from the drilling location to transport the shuttle suture. Should the connection system fail or the shuttle suture become disengaged from the drill guide during the retrieval, a repositioning and possible second drilling step would be needed to transport the shuttle suture, costing unnecessary surgical steps, surgical time, and possible harm to the patient.

In many cases the user may acquire a preoperative x-ray image of the pathology but may not have access to intraoperative visualization. Current devices are not enabled to provide the user an intraoperative measurement of the reduction distance, which limits the accuracy of the reconstruction, or requires the user to employ a separate measurement device, adding surgical steps and time to complete the procedure.

A further limitation of the current marketed devices is the complexity of the assemblies contributing to a higher device cost as the number of components in the assembly increases. Another drawback of a complex assembly is the increased opportunity for bacterial contamination in the small crevices between components, making the device difficult to sterilize. Therefore, a clear need exists for a solution to the aforementioned problems.

BRIEF SUMMARY OF THE INVENTION

In one embodiment of the invention a surgical guide system is provided, comprising a guide body having a receiver and a reference plate joined by a connecting arm, a portion of the receiver and a portion of the reference plate intersecting a guide axis, the guide body operable for at least one bone to be interposed between the receiver and reference plate, the receiver comprising a tubular body having a proximal end and a distal end, and an adjustment aperture formed through the receiver from the proximal end to the distal end, and a guide sleeve comprising a tubular body having a proximal end and a distal end, the proximal end operable for coupling with the receiver within the adjustment aperture, wherein a rotation of the guide sleeve with respect to the receiver causes a change in distance between the guide sleeve and the reference plate, and the lumen of the guide sleeve is operable to guide a surgical instrument along the guide axis therethrough, and the guide axis intersects at least one surface of the at least one bone interposed between the receiver and the reference plate during use. Also in one embodiment, the guide sleeve is recessed below the proximal surface of the receiver and may further include a locating member comprising a tubular body having a proximal end and a distal end; and a reference arm extending from the distal end of the tubular body having a portion offset from said guide axis, wherein the locating member is rotatable on the guide sleeve, and a portion of the reference arm is operable to contact a portion of a first surface on the at least one bone interposed between the receiver and the reference plate, the guide axis intersecting a second surface on the at least one bone. Also in one embodiment, the receiver further comprises a scale calibrated to provide a measurement of the distance between the guide sleeve and the reference plate when a designated feature of the of the drill sleeve and the scale are both in view. Also in one embodiment, the connecting arm further comprising a channel operable to contain a portion of a shuttle cable, wherein at least a portion of the shuttle cable is recessed below the outer surface of the connecting arm. Also in one embodiment the reference plate may further comprise at least one orientation aperture operable for containing a shuttle cable for engagement with a surgical device. Also in one embodiment, the guide body further comprises at least one retainer groove, wherein the groove is operable to secure a portion of the shuttle cable. Also in one embodiment, the reference plate further comprises an aperture operable to receive a surgical instrument and may further also include a slot formed from the proximal surface to the distal surface. Also in one embodiment, the surgical guide may include a shuttle cable, wherein a first portion of the shuttle cable is coupled to reference plate and at least a second portion is coupled to the receiver or features extending from the receiver, wherein at least a third portion of the shuttle cable is configured on the reference plate for engagement with a surgical tool. The surgical guide system may also include a driver operable to couple with the guide sleeve, wherein a torque applied to the driver causes the guide sleeve to rotate.

In another aspect of the invention, a method of transporting a shuttle cable through bone tissue is provided comprising the steps: (a) positioning the surgical guide system of any of the previous claims on at least one bone, the bone the having a first side and a second side, wherein the bone is interposed between the receiver and the reference plate, the receiver being on the first side of the bone and the reference plate being on the second side, wherein the guide axis intersects a hole formed in the bone, wherein the surgical guide system has a portion of a shuttle cable coupled to the reference plate configured for engaging a surgical tool, the shuttle cable having a first end and a second end, (b) guiding a surgical tool through the hole in the at least one bony structure from the first side to the second side, (c) engaging the surgical tool with a portion of the shuttle cable, (d) retrieving a first end of the shuttle cable through the hole from the second side of the bone to the first side, and (e) moving the guide body away from the bone, wherein one end of the shuttle cable is available for manipulation on the first side of the hole, and a second end of the flexible member is available for manipulation on the second side of the hole, and a portion of the flexible member passes through the hole. Also in one embodiment, the method further comprises the step of forming a hole in at least one bone from a first side to a second side, wherein the hole is collinear with the guide axis.

BRIEF DESCRIPTION OF THE DRAWINGS

The foregoing and other objects, features, and advantages will be apparent from the following more elaborate description of the embodiments, as illustrated in the accompanying drawings in which like reference characters refer to the same parts throughout the different views. The drawings are not necessarily to scale, emphasis instead being placed upon illustrating the principles of the embodiments. For a detailed description of example embodiments, reference will now be made to the accompanying drawings in which:

FIGS. 17A-17B illustrate close-up views of an alternative embodiment of the drill guide body of FIG. 1, in accordance with the disclosure;

FIGS. 17C-17D illustrate close-up views of the drill guide body of FIGS. 17A-17B integrated with a shuttle suture, in accordance with the disclosure;

FIGS. 18A-18C illustrate exemplary steps for integrating a shuttle suture onto the drill guide body of FIGS. 17A-17B, in accordance with at least one embodiment disclosed;

FIGS. 21A-21B illustrate close-up views of the drill guide body of FIGS. 20A-20B integrated with a shuttle suture, in accordance with the disclosure;

FIGS. 22A-22D illustrate exemplary use steps for placing a guide, forming an aperture, and retrieving a shuttle suture through said aperture, in accordance with at least one embodiment disclosed;

FIGS. 23A-23C illustrate perspective and close-up views, respectively, of an alternative embodiment of the drill guide body of FIGS. 13A-13D, in accordance with the disclosure;

FIG. 24 illustrates exemplary steps for integrating a shuttle suture onto the drill guide body of FIGS. 23A-23C, in accordance with the disclosure;

FIGS. 25A-25B illustrate bottom views of the drill guide body of FIGS. 23A-23C integrated with a shuttle suture, in accordance with the disclosure;

FIGS. 26A-26B illustrate perspective and side views, respectively, of an alternative embodiment of the drill guide body of FIGS. 13A-13D, in accordance with the disclosure;

FIG. 27 illustrates exemplary steps for integrating a shuttle suture onto the drill guide body of FIGS. 26A-26B, in accordance with the disclosure.

Figure 1:
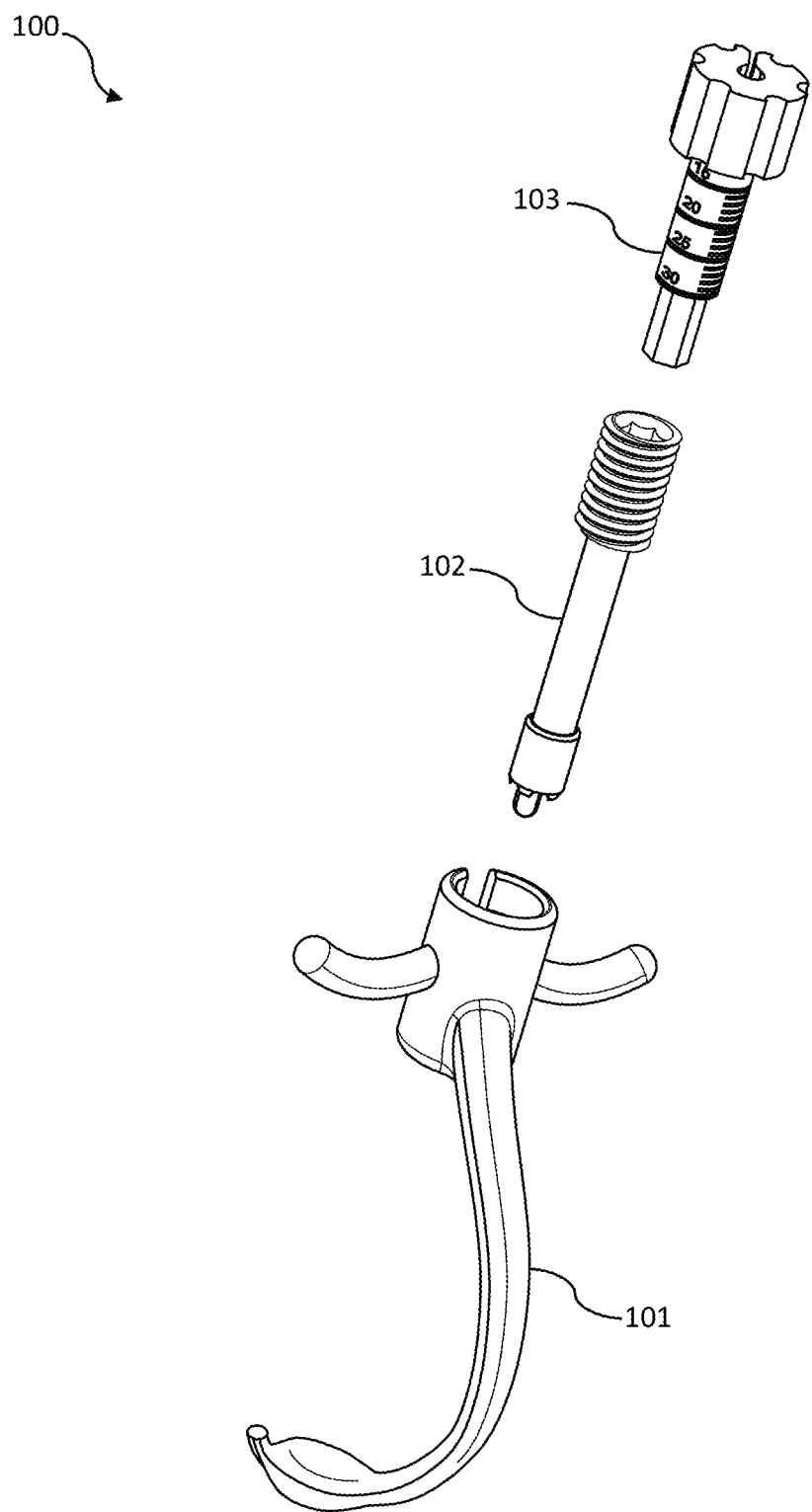
FIG. 1 is a perspective view of an adjustable, depth-limiting drill guide system, according to an embodiment of the present invention.
Figure 2:
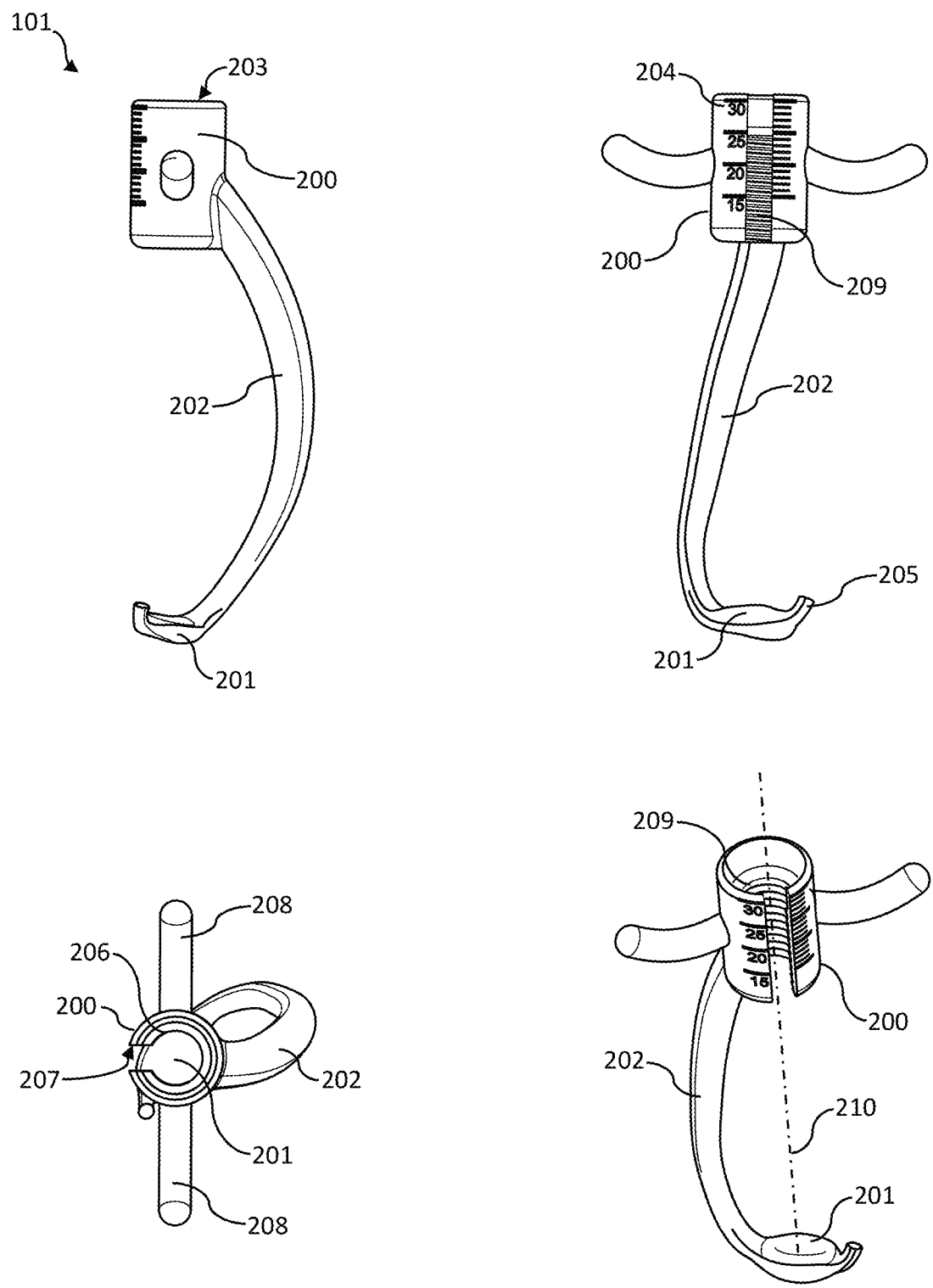
FIG. 2 illustrates side, front, top, and perspective views, respectively, of the drill guide body from FIG. 1, in accordance with the disclosure.
Figure 3:
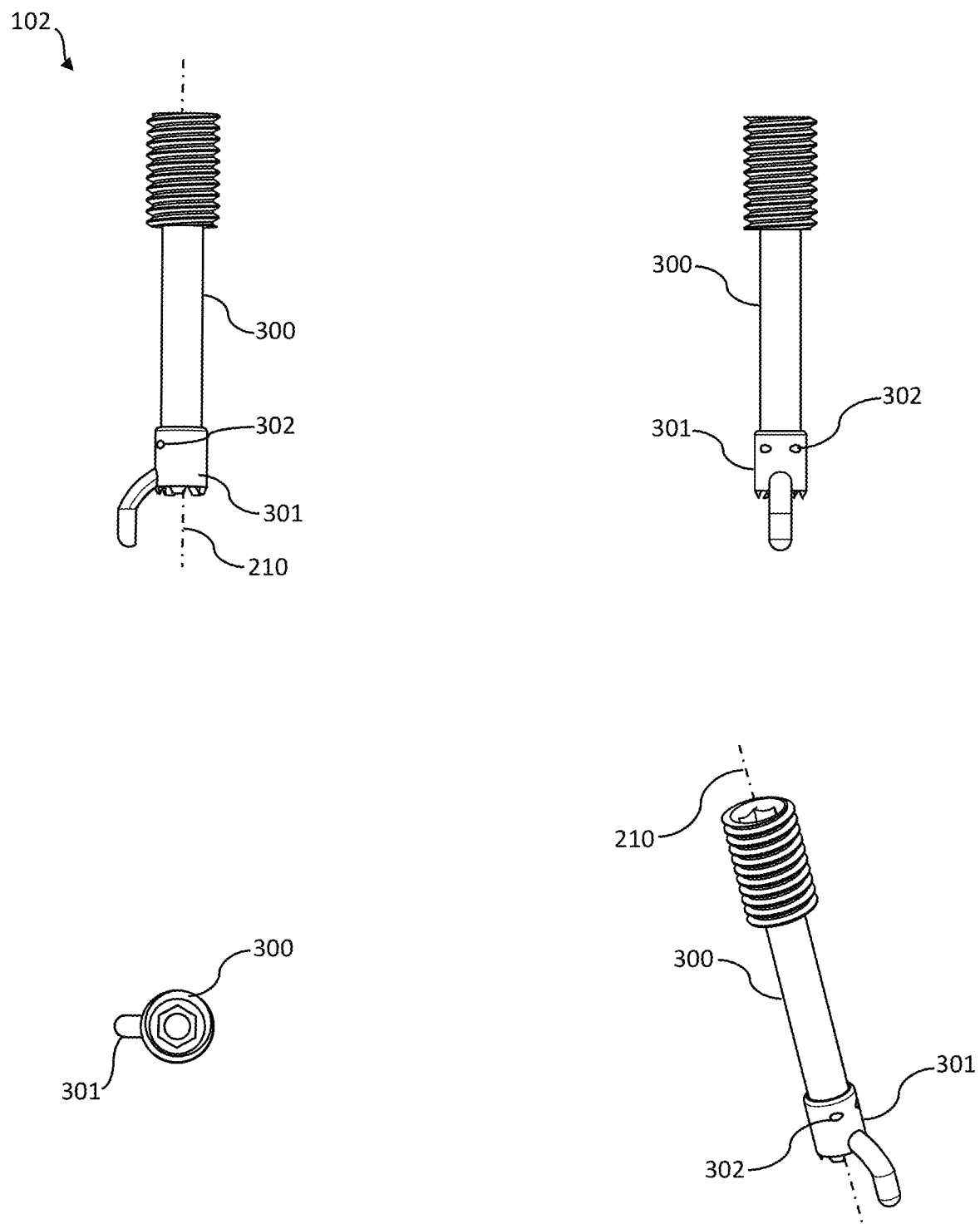
FIG. 3 illustrates perspective, front, side, and top views, respectively, of the guide sleeve assembly of FIG. 1, in accordance with the disclosure.

While the invention is amenable to various modifications, permutations, and alternative forms, specific embodiments have been shown by way of example in the drawings and are described in detail below. The intention, however, is not to limit the invention to the embodiments described. The invention is intended to cover all modifications, equivalents, and alternatives falling within the scope of the invention as defined by the appended claims.

DETAILED DESCRIPTION

The inventor provides a unique adjustable and depth-limiting drill guide system for safely forming apertures in bone tissue during surgical reconstruction procedures. The drill guide system may also provide capability to allow the user to retrieve a shuttle suture or wire through a formed aperture thereby connecting the formed aperture to an auxiliary surgical portal for the transfer of other surgical devices. The present invention is described in enabling detail in the following examples, which may represent more than one embodiment of the present invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Referring now to FIG. 1, one embodiment of an adjustable, depth-limiting guide system 100 is shown in an exploded view. In this example, guide system 100 is comprised of a guide body 101, a guide sleeve 102 adjustable within guide body 101, and a driver 103. The components of guide system 100 may be manufactured using standard machining techniques, moulding processes, casting processes, additive manufacturing or other methods using biocompatible materials suitable for surgical instrumentation. These materials include, but are not limited to alloys of stainless steel, alloys of titanium, thermoplastics such as polyphenyl sulfone (PPSU), polyoxymethylene (acetal), polyether-etherketone (PEEK), or fiber-reinforced composites using thermoset or thermoplastic resins.

FIGS. 2A-2D are side, front, top, and perspective views, respectively, of guide body 101 which is comprised of a receiver 200 formed at the proximal end, a reference plate 201 formed at the distal end, and a connecting arm 202. Receiver 200 is an elongate, tubular body having an adjustment aperture 206 formed collinear with a guide axis 210 which intersects reference plate 201, and a thread form 209 functional along the inner diameter of adjustment aperture 206 for adjusting the axial position of guide sleeve 102 in receiver 200. A depth limiting surface 203 forms one end of guide body 101 having a known distance from reference plate 201. Incorporated into receiver 200 is a slot 207 functioning to allow passage of elements of guide sleeve 102 which exceed the inner diameter of adjustment aperture 206, and to allow visualization of the position of guide sleeve 102 relative to depth limiting surface 203. A scale 204 may be incorporated on the outer surface of receiver 200 in proximity to slot 207 providing the user a distance measurement between reference plate 201 and the distal end of guide sleeve 102. A handle 208 may extend radially from the sides receiver 200 enabling manipulation of guide body 101 during positioning.

Connecting arm 202 is an elongate body which extends from the outer surface of receiver 200 distally providing a rigid connection to reference plate 201 and shaped to allow for a bone or a plurality of bones tissue to be interposed between receiver 200 and reference plate 201. It should be noted that the curvature of connecting arm 202 should not limited to the example illustrated but may be shaped advantageously to enable various orientations, positions to encompass a variety of bony shapes. In this example, reference plate 201 is a generally flat oval body having a proximal surface and a distal surface and is shaped advantageously to conform to the tissue surface it is designed to oppose. A probe 205 may extend from the distal end of reference plate 201 to provide the user with tactile feedback of tissue shape during the positioning of guide body 101.

FIGS. 3A-3D illustrate perspective, front, side, and top views, respectively, of guide sleeve 102, according to one embodiment of the present invention. Guide sleeve 102 comprises a guide sleeve body 300, a locating member 301, and a retaining pin 302. Locating member 301 is designed to provide a mechanical reference from the edge of a bone surface to guide axis 210 and is operable to freely rotate on the distal end of guide sleeve body 300.

Figure 4:
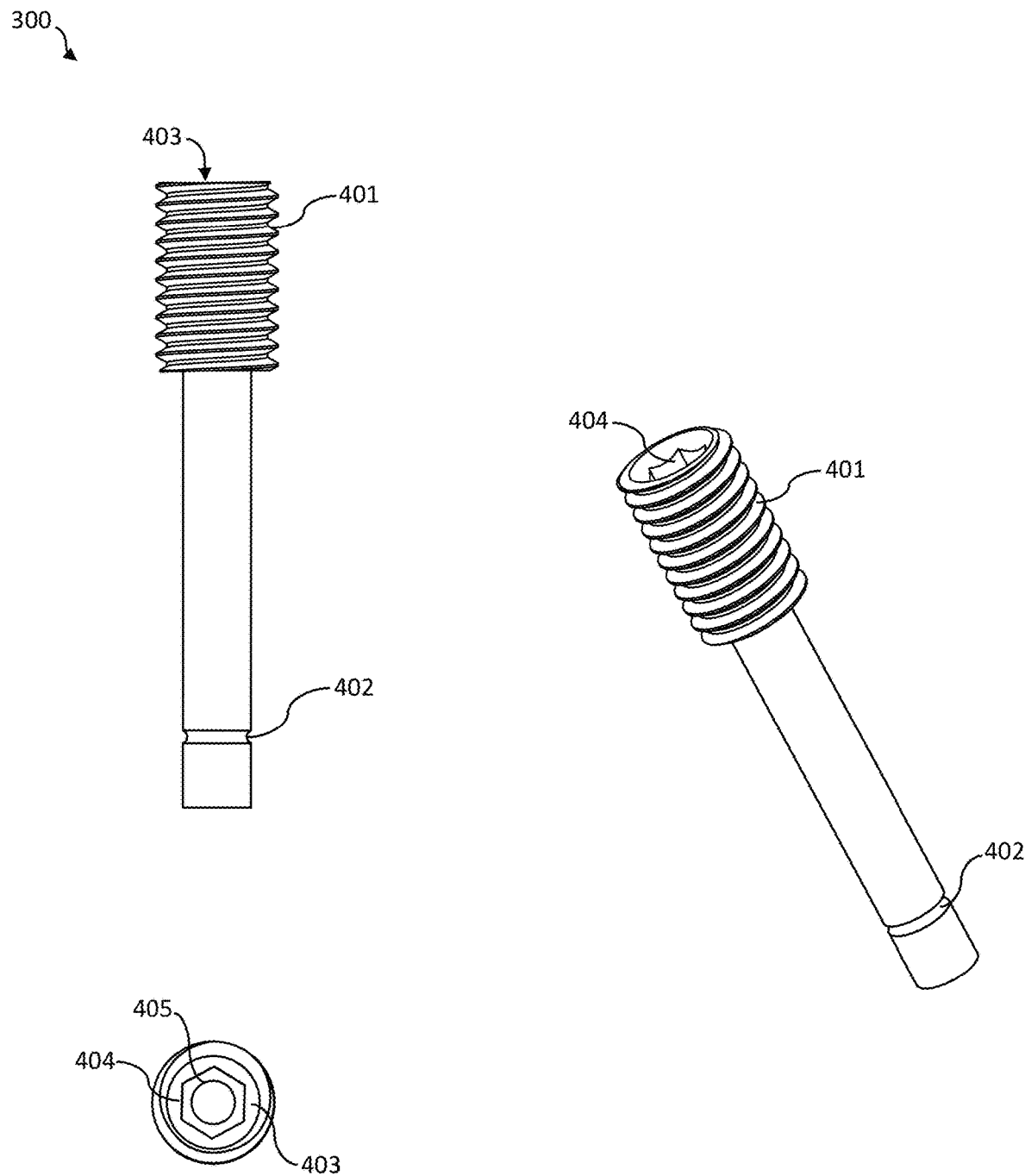
FIG. 4 illustrates front, top, and perspective views, respectively, of the drill guide sleeve from FIGS. 3A-3D, in accordance with the disclosure.
Figure 5:
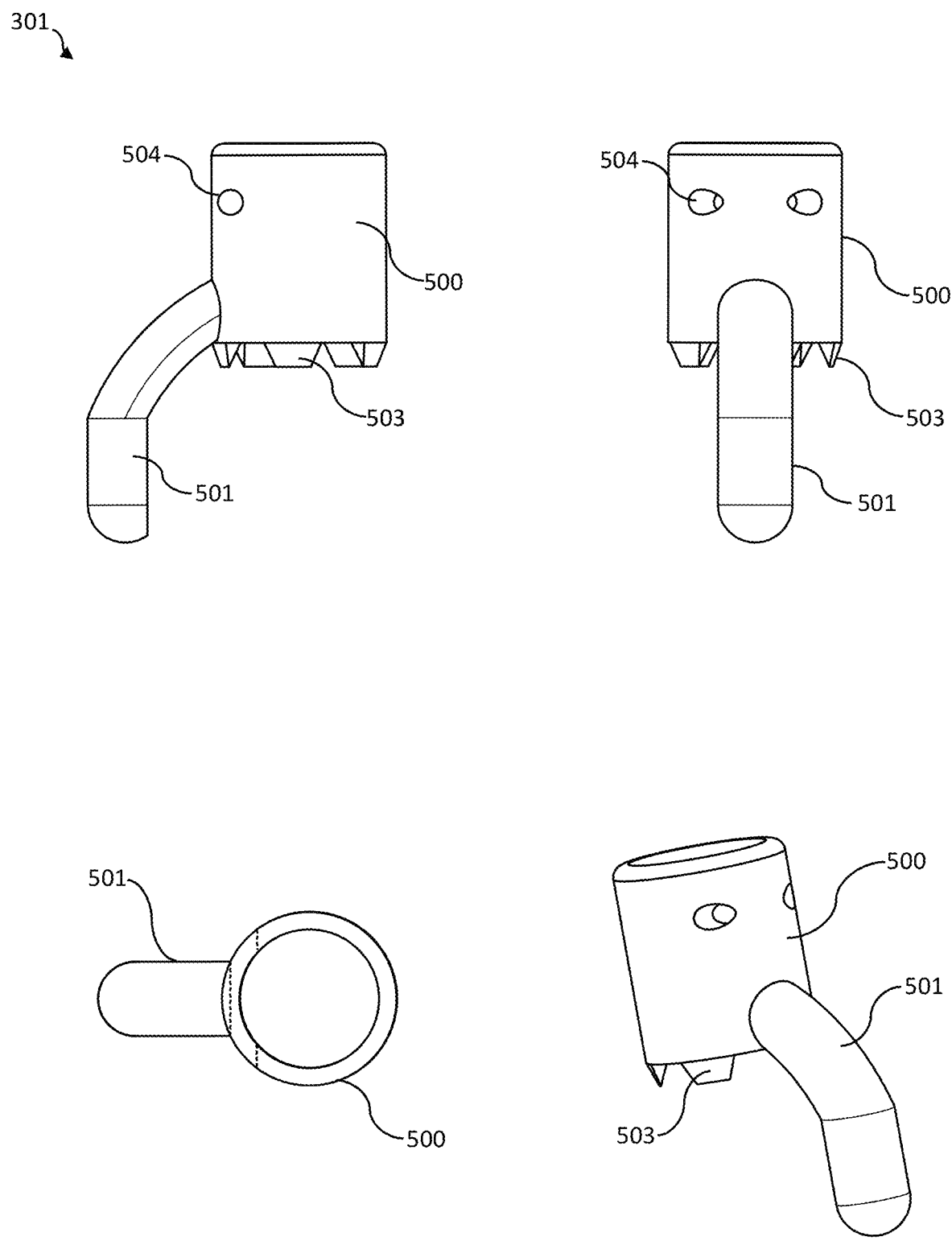
FIG. 5 illustrates front, side, top, and perspective views, respectively, of the offset spacer from FIGS. 3A-3D, in accordance with the disclosure.

FIGS. 4A-4C are front, top, and perspective views, respectively, of guide sleeve body 300, in accordance with the disclosure. In this example, guide sleeve body 300 is a tubular body, designed for adjustable engagement with guide body 101, having a reference surface 403 at its proximal end with the distal end designed for engagement with a bone surface. A drill aperture 405 is formed in guide sleeve body 300 and may be dimensioned to accept and guide a drill or other instrument therethrough. A thread form 401 is incorporated in the proximal end to engage and allow adjustment within receiver 200 (not shown). A female hex drive 404 is formed in proximal end of guide sleeve body 300. A retaining groove 402 is formed at the distal end designed to accept retaining pin 302 (not shown).

FIGS. 5A-5D are front, side, top, and perspective views, respectively, of locating member 301, according to one embodiment of the present invention. Locating member 301 is comprised of a tubular barrel 500 having a proximal end and a bone contacting end, and an reference arm 501. Barrel 500 has an inner diameter dimensioned to accept the distal end of guide sleeve body 300 with a sliding fit. A plurality of traction spikes 503 are formed on the bone-contacting face of barrel 500 to improve grip on the bone surface, minimizing the translation of guide sleeve 102 (not shown) from the desired position on the bone surface. Reference arm 501 may extend radially and distally from the outer diameter of barrel 500 at the bone-contacting end. When in operation, reference arm 501 is opposed to a bone surface, enabling guide sleeve 102 (not shown) to be positioned at a pre-set distance from the edge of the bone. Additionally, a pin retaining hole 504 is formed at the proximal end of barrel 500.

Figure 6:
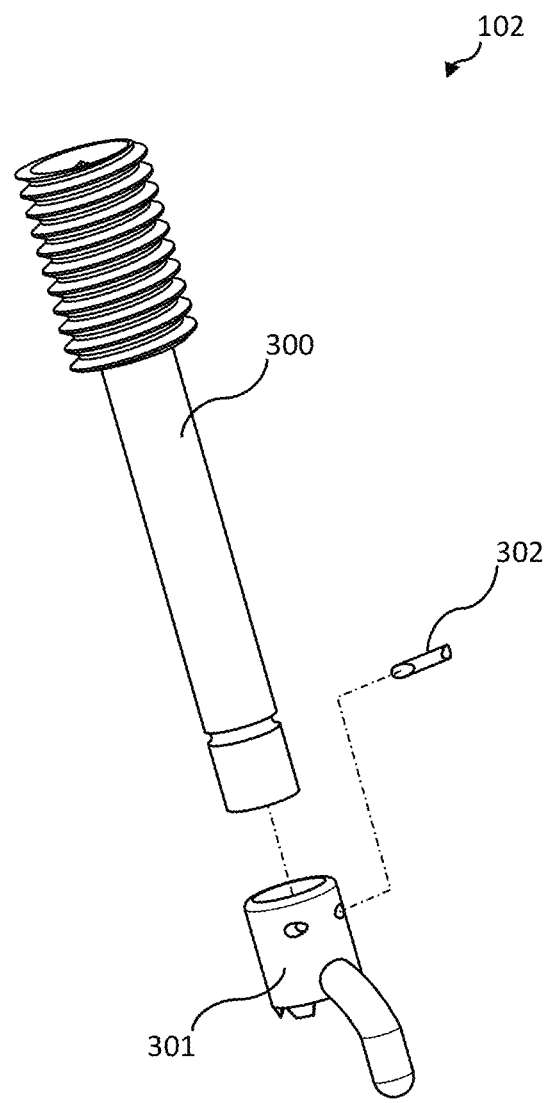
FIG. 6 is an exploded view of the guide sleeve assembly of FIG. 1, in accordance with the disclosure.
Figure 7:
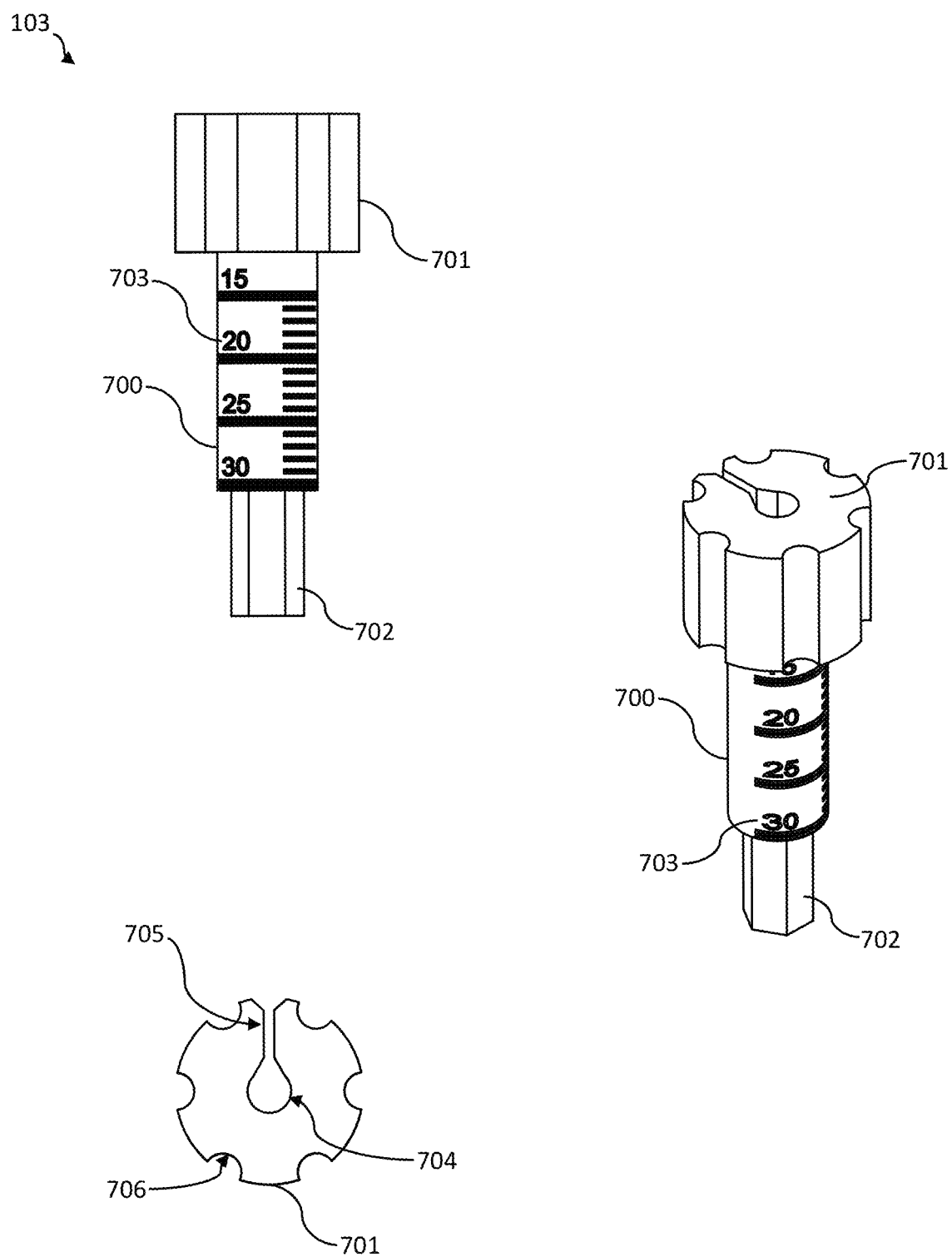
FIG. 7 illustrates front, back, bottom, and perspective views, respectively, of the guide sleeve driver of FIG. 1, in accordance with the disclosure.

FIG. 6 is an exploded view of guide sleeve 102, according to one embodiment of the present invention. In this illustration, guide sleeve body 300, locating member 301, and retaining pin 302 are shown aligned for assembly.

FIGS. 7A-7D are front, top, and perspective views, respectively, of driver 103, according to one embodiment of the present invention. In this example, driver 103 is comprised of a tubular driver body 700 with an operating knob 701 formed at the proximal end and a male hex drive 702 at the distal end. Male hex drive 702 is designed to couple with and enable the user to rotate guide sleeve body 300 (not shown) when adjustment is required. A central aperture 704 and a slot 705 formed from the proximal end to the distal end operable to allow passage for flexible wires or shuttle sutures to the interior of central aperture 704. A calibrated scale 703 may be marked on the outer surface of driver body 700 providing the user a second indication of the between reference plate 201 (not shown) and the distal end of guide sleeve 102 (not shown). A plurality of traction grooves 706 may be formed in operating knob 701 for improved grip for the user during operation.

Figure 8B:
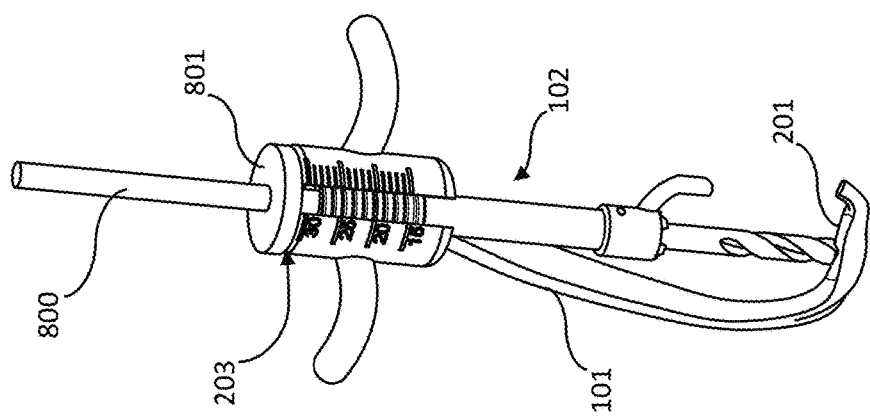
FIGS. 8A-8B illustrate the depth-limiting function of the drill guide body of FIG. 1, according to an embodiment of the present invention.
Figure 8A:
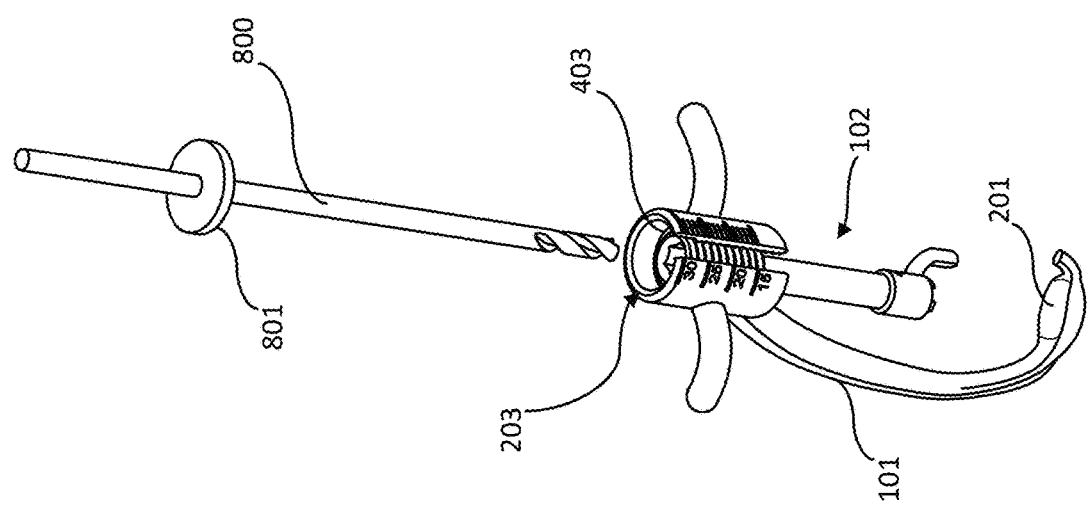

FIGS. 8A-8B illustrate the depth-limiting function of guide system 100, according to an embodiment of the present invention. FIG. 8A illustrates a drill 800 having a mechanical depth stop 801 formed at a distance from the cutting end of drill 800 calibrated to the distance between depth limiting surface 203 and reference plate 201. Drill guide 102 is coupled with guide body 101 and adjusted such that reference surface 403 is recessed below depth limiting surface 203. As shown in FIG. 8B, when drill 800 is advanced through guide sleeve 102, depth stop 801 will contact depth limiting surface 203 and prevent further advancement of drill 800 into reference plate 201.

Figure 9A:
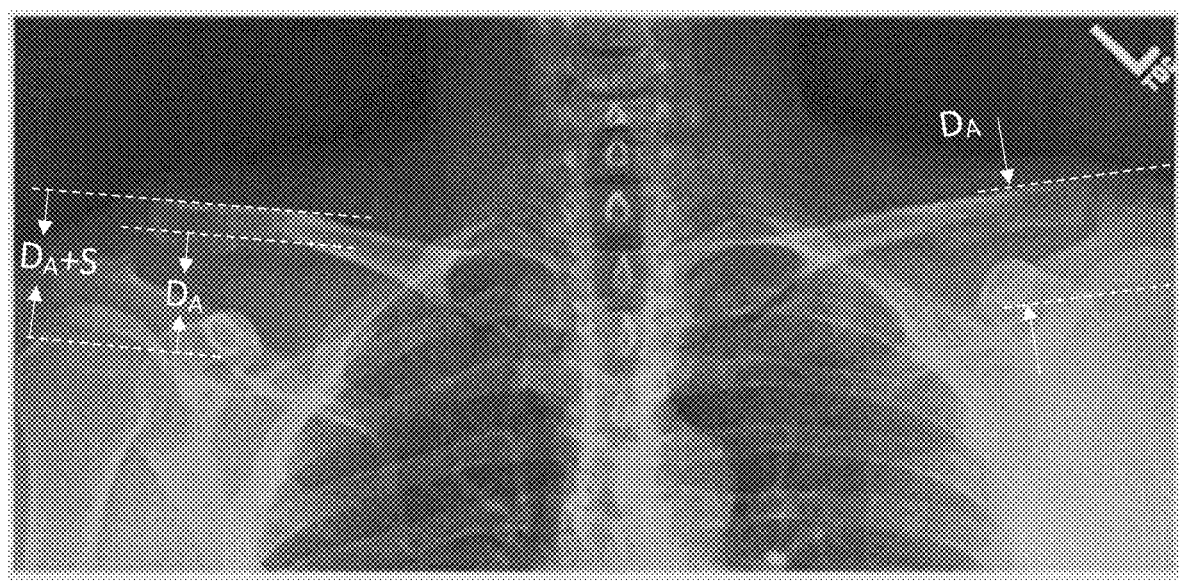
FIG. 9A is an x-ray image of the superior human torso illustrating an acromioclavicular separation of the right shoulder with the left shoulder unaffected, in accordance with the disclosure.
Figure 9B:
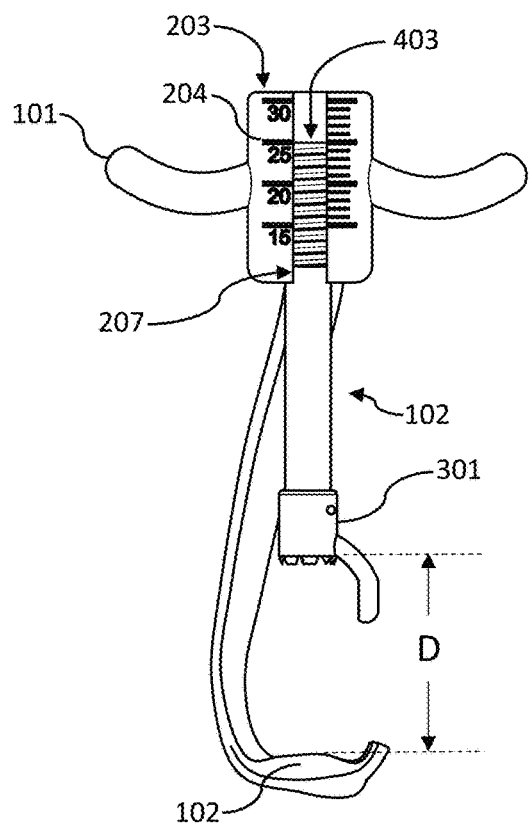
FIG. 9B illustrates the use of an integrated drill depth measurement scale, according to an embodiment of the present invention.

FIGS. 9A-9B illustrate the exemplary use of scale 204, according to an embodiment of the present invention. FIG. 9A is a pre-operative x-ray image of the superior human torso illustrating an acromioclavicular separation of the right shoulder with the left shoulder the unaffected side. A measurement can be made from the inferior aspect of the coracoid process to the superior aspect of the clavicle as shown. The normal, anatomical measurement, $D_A$, taken on the unaffected side, can be compared to the affected side, measures as $D_{A+S}$, where S represents the separation distance added to the normal anatomical distance of the unaffected side. For this example, the ideal bone aperture for reconstruction should be made when the affected side has been reduced from the displaced distance, $D_{A+S}$, to the anatomical distance, $D_A$. FIG. 9B shows guide body 101 with guide sleeve 102 adjusted such that reference surface 403 is recessed below depth limiting surface 203. A distance measurement reading can be made when reference surface 403 is viewed through slot 207 and compared to the calibrated markings on scale 204. The indicated distance will correspond with the distance, D, between the bone-contacting side of locating member 301 and the proximal surface of reference plate 201.

FIGS. 10A-10F illustrate exemplary steps for placing and drilling through bone tissue using guide system 100, according to an embodiment of the present invention. In this example, guide system 100 is used to reduce an acromioclavicular separation and form an aperture through a clavicle 1000 and a coracoid 1001 interposed between receiver 200 and reference plate 201, while the clavicle is maintained in its reduced position by guide system 100.

Figure 10B:
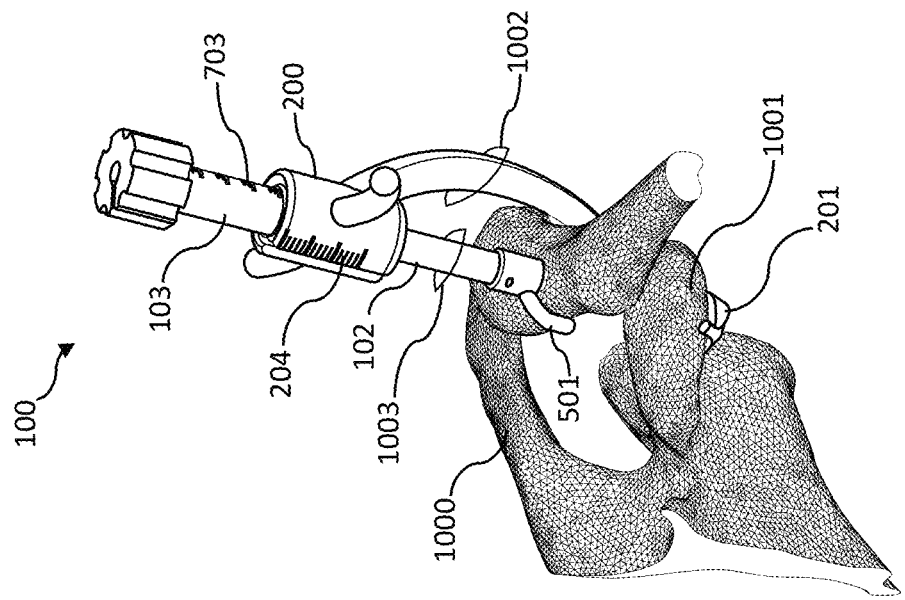
FIGS. 10A-10F illustrate exemplary steps for the placement of the drill guide system of FIG. 1 onto bony structures to form a bone tunnel, in accordance with at least one embodiment disclosed.
Figure 10A:
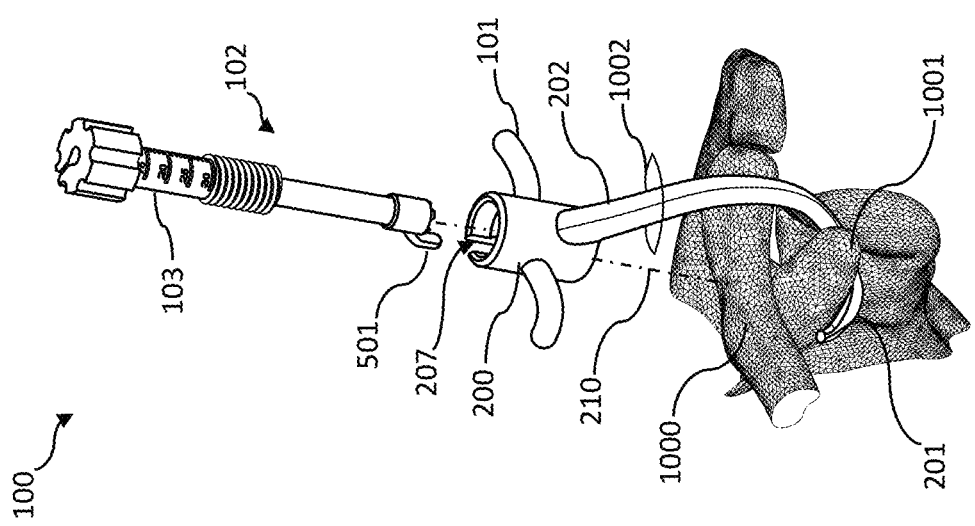
Figure 10D:
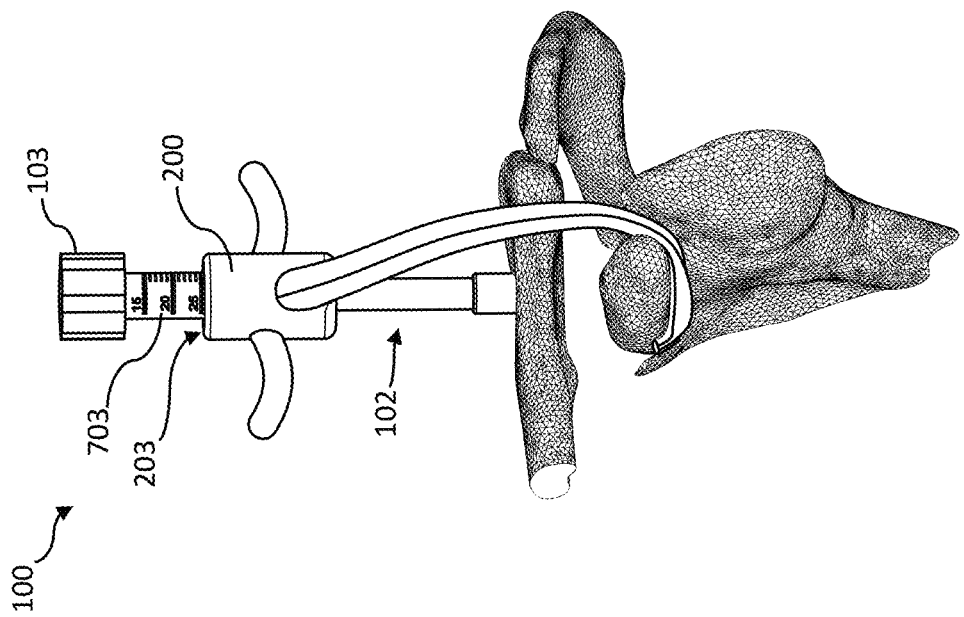
Figure 10C:
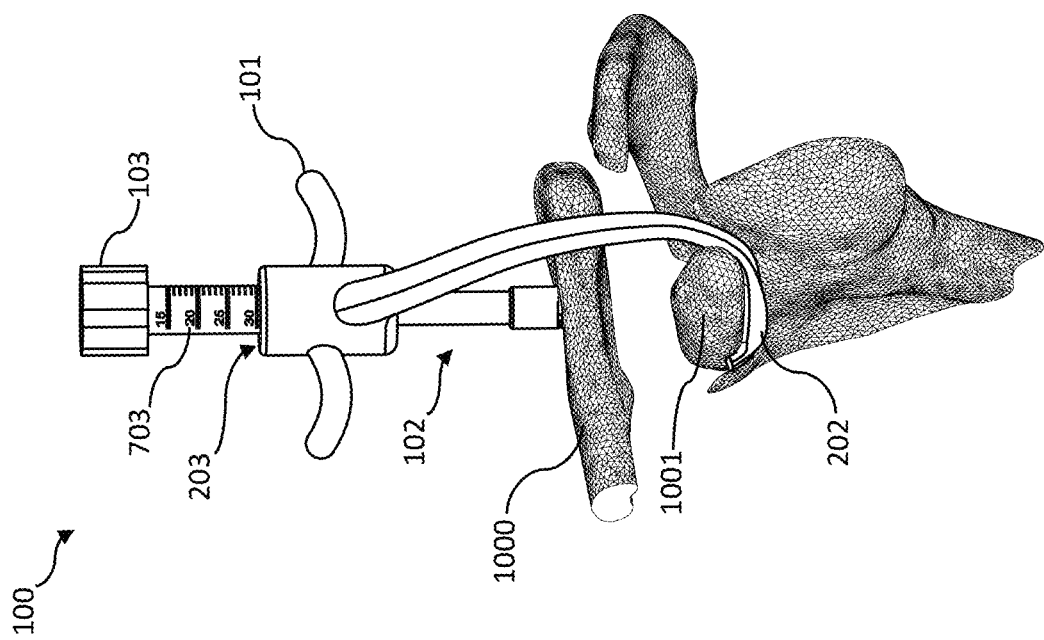
Figure 10F:
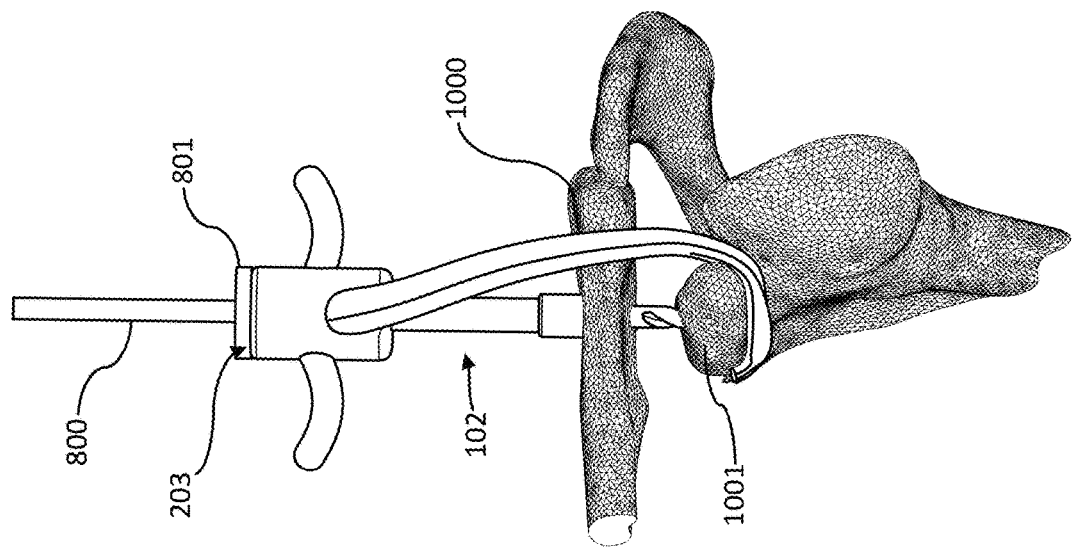
Figure 10E:
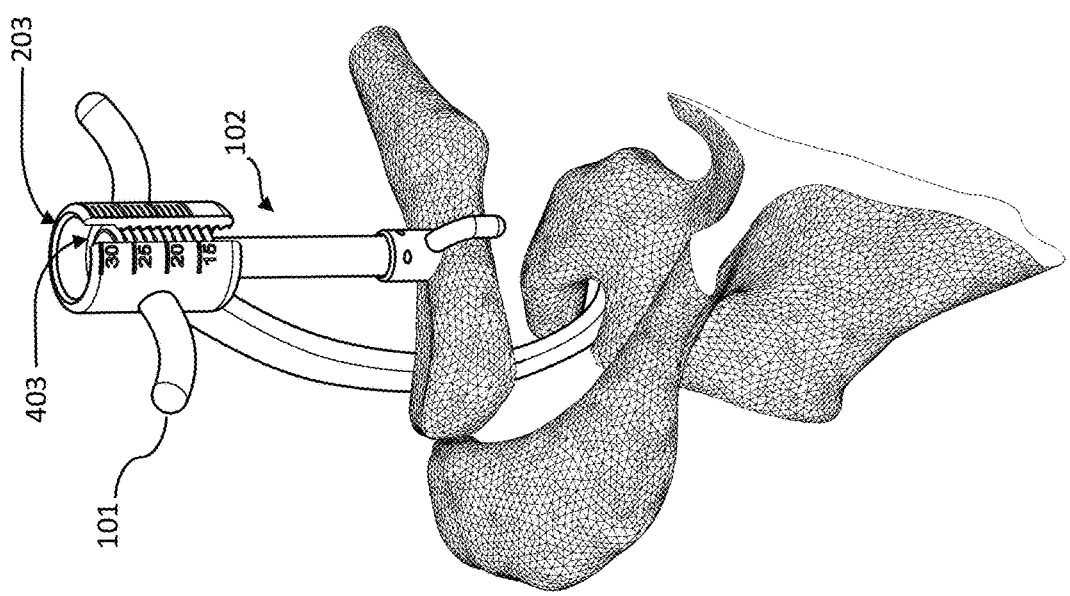

FIG. 10A shows guide body 101 placed such that reference plate 201 is located opposing the inferior aspect of coracoid 1001 by extending connecting arm 202 through a first surgical portal 1002 anterior to clavicle 1000 and medial to the acromioclavicular joint. Also illustrated is guide sleeve 102 coupled with driver 103 and aligned for coupling with receiver 200. Reference arm 501 is aligned with slot 207 enabling guide sleeve 102 to be introduced into receiver 200 along guide axis 210. FIGS. 10B-10C illustrate guide system 100 placed in the desired surgical location with the bone-contacting end of guide sleeve 102 approximated to the superior aspect of clavicle 1000 with reference arm 501 approximated to the posterior aspect of clavicle 1000 accomplished by advancing the distal end of guide sleeve 102 through receiver 200 and a second surgical portal 1003 by a rotation of driver 103. In this position, the injured joint is ready for reduction and a joint separation measurement can be made using scale 703, if viewed from the anterior, or scale 204 if viewed from the posterior, to confirm the separation distance, $D_{A+S}$, previously identified on the patient's pre-operative x-ray. The measurement from scale 703 is acquired by referencing the indicated mark which is aligned to depth limiting depth limiting surface 203 when driver 103 is mated to guide sleeve 102 as shown in FIG. 10C. FIG. 10D illustrates guide system 100 in its adjusted position viewed from the posterior. The acromioclavicular joint is reduced by turning driver 103 and advancing guide sleeve 102 through receiver 200 until scale 703 indicates the desired distance, $D_A$, which may be confirmed with an intra-operative x-ray if needed. In this configuration the tissue has been realigned to its anatomical position and the aperture in the bone can then be formed. FIG. 10E illustrates guide body 101 and guide sleeve 102 positioned for drilling with driver 103 (not shown) removed from the assembly and reference surface 403 recessed below depth limiting surface 203. FIG. 10F illustrates the depth-limited drilling step. Drill 800 is introduced into guide sleeve 102 and advanced until depth stop 801 contacts depth limiting surface 203, thereby forming an aperture through both clavicle 1000 and coracoid 1001.

Figure 11A:
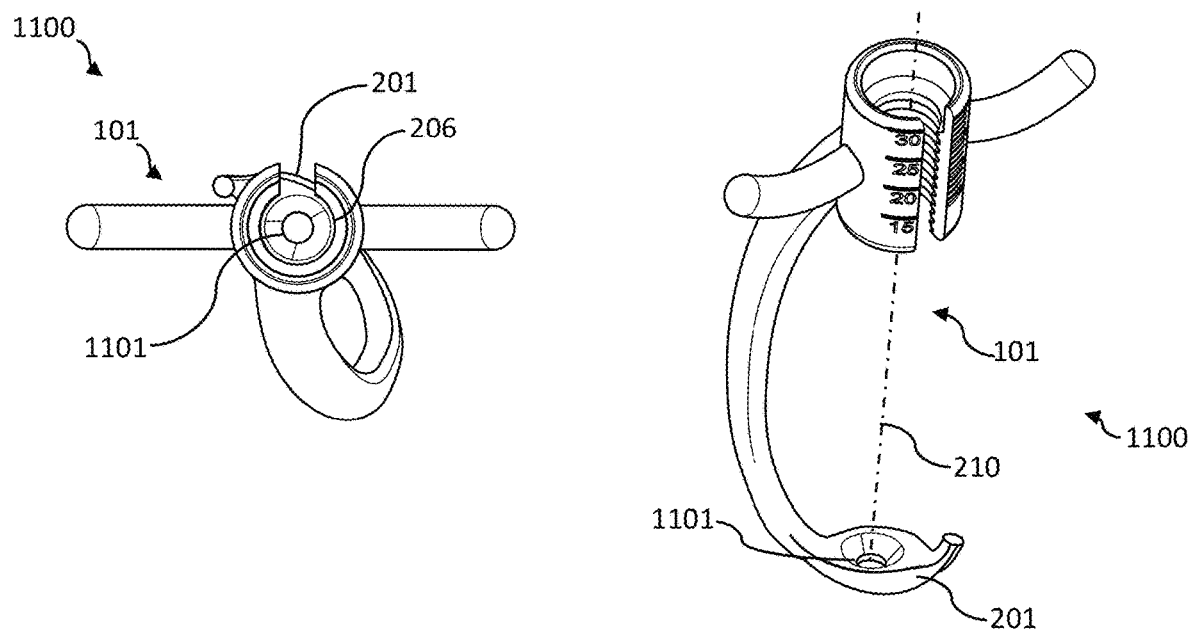
FIG. 11A illustrates perspective and top views, respectively, of an alternative embodiment of the drill guide body of FIG. 1, in accordance with the disclosure.
Figure 11B:
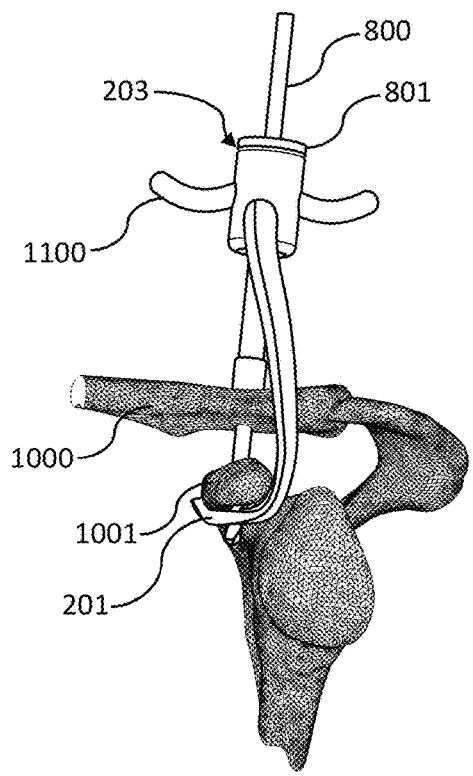
FIG. 11B is a perspective view of the depth-limited drilling step, in accordance with at least one embodiment disclosed.

FIG. 11A shows top and perspective views, respectively, of a guide body 1100, according to an embodiment of the present invention. In this example, an guide aperture 1101 has been formed in reference plate 201 collinear with guide axis 210 and having a diameter to provide a slip fit with drill 800 (not shown). FIG. 11B further illustrates the depth-limiting capability of guide body 1100. The user may need to verify the completed drilling of the bone tissue and may choose to visualize the cutting end of drill 800. Depth stop 801 may be positioned on drill 800 such that when depth stop 801 is advanced to approximate depth limiting surface 203, a portion of the cutting end of drill 800 exits the distal side of reference plate 201 through guide aperture 1101 and can be visualized providing the user with a confirmation of complete drilling and enable other instruments to be passed through clavicle 1000 to arrive on the distal side of coracoid 1001 and available for manipulation by the user.

Figure 12C:
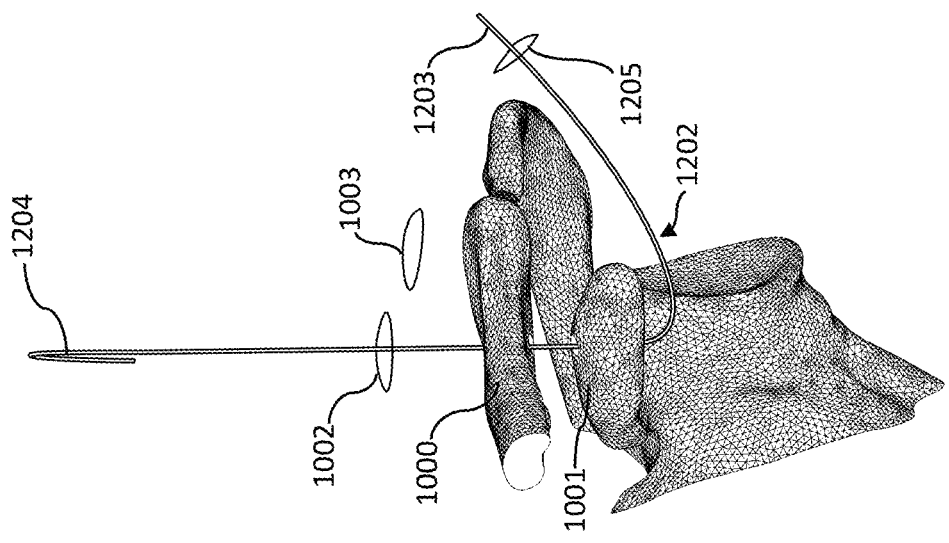
FIGS. 12B-12C illustrate exemplary use steps of the embodiment of the drill guide body of FIG. 12A, in accordance with the disclosure.
Figure 12B:
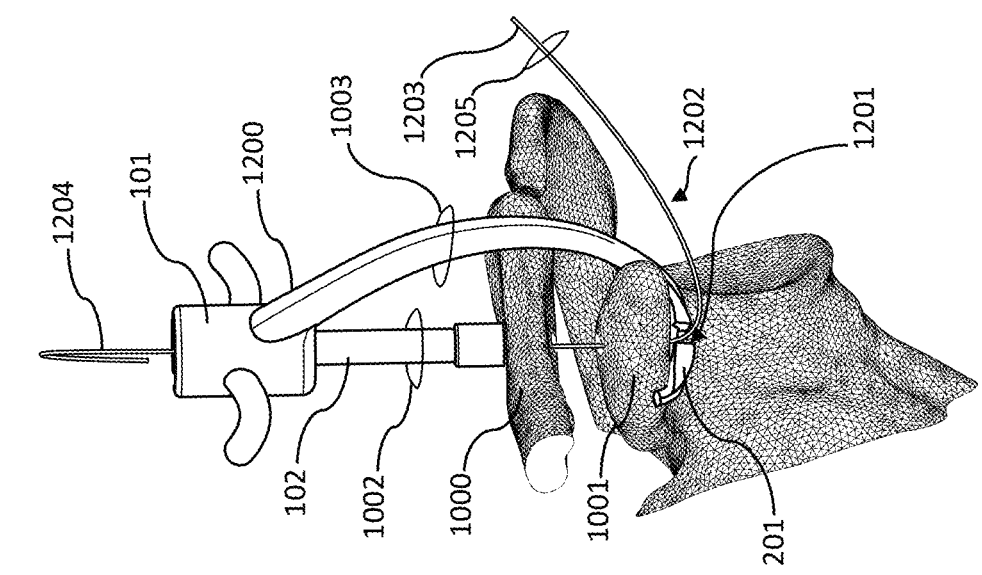
Figure 12A:
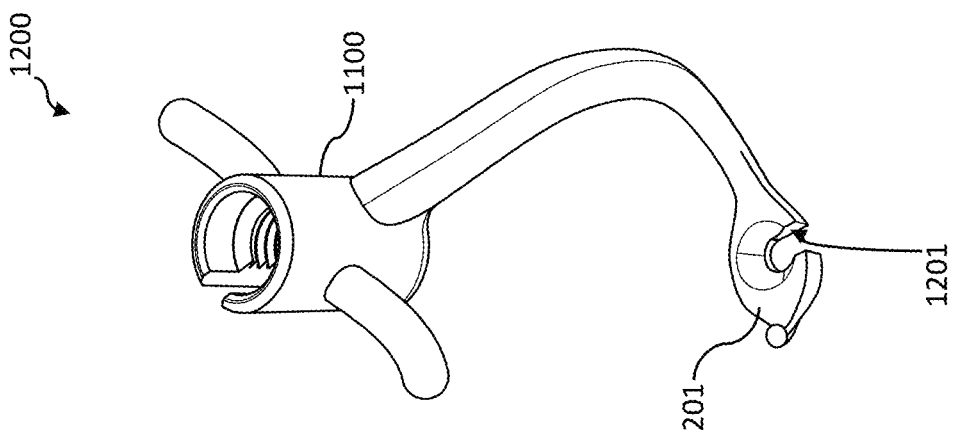
FIG. 12A illustrates an alternative embodiment of the drill guide body of FIG. 1, in accordance with the disclosure.

FIG. 12A illustrates a perspective view of a guide body 1200, according to another embodiment of the present invention. In this example, a slot 1201 has been formed in reference plate 201 of guide body 1100. Slot 1201 allows wires, shuttle sutures, or other surgical instrumentation passed through the bone aperture to be dissociated from reference plate 201 and transferred to a different surgical portal than used by connecting arm 202. FIGS. 12B-12C illustrate exemplary use steps of drill guide body 1200. After forming the bone aperture, a portion of a shuttle cable 1202 may be passed through guide sleeve 102, clavicle 1000, coracoid 1001, and extend distally from reference plate 201. Shuttle cable 1202 is shown as a flexible member having a first end 1203 and a second end 1204 and may consist of a surgical suture, braid, wire, tape, or other device operable to connect to surgical instruments or implants and for transport through tissue. End 1203 is passed through to the distal side of coracoid 1001 assembly while end 1204 is retained on the proximal side of guide body 101. End 1203 is separated from reference plate 201 via slot 1201 and may then be transferred to exit an auxiliary surgical portal 1205 enabling guide body 1200 to be removed from surgical portal 1003 independently.

FIGS. 13A-13D illustrate perspective and close-up views, respectively, of a guide body 1300, according to another embodiment of the present invention. In this example, several features are formed in guide body 1200 to enable the connection of shuttle cable 1202 enabling the transfer of its ends to surgical portals by using guide body 1300 as the transport mechanism.

Figure 13A:
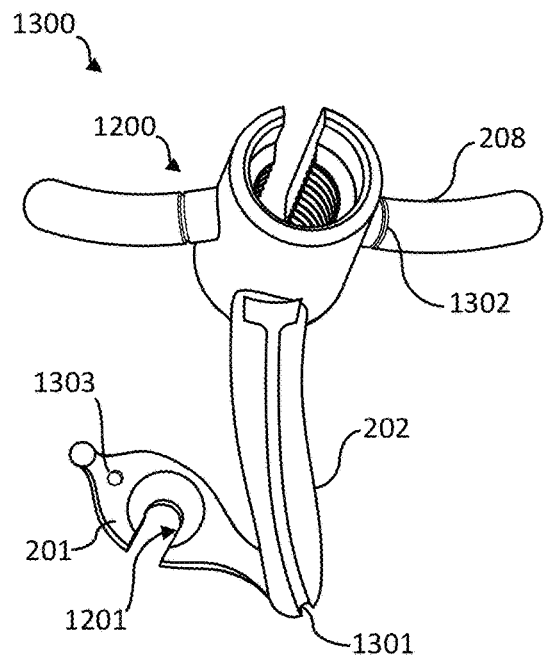
FIGS. 13A-13D illustrate perspective and close-up views, respectively, of an alternative embodiment of the drill guide body of FIG. 1, in accordance with the disclosure.
Figure 13B:
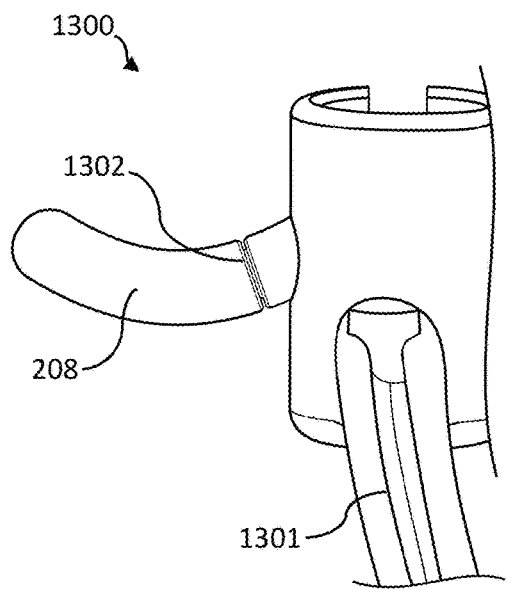
Figure 13C:
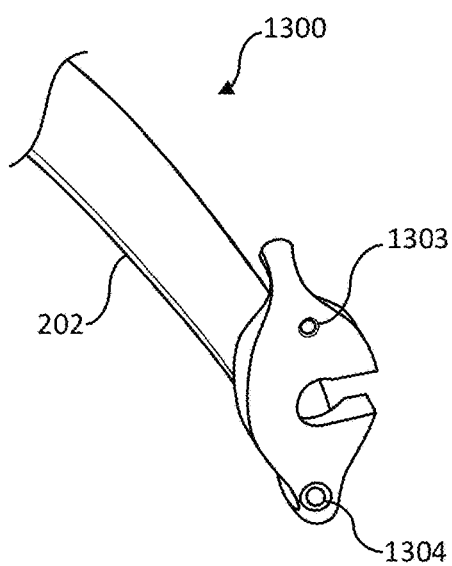
Figure 13D:
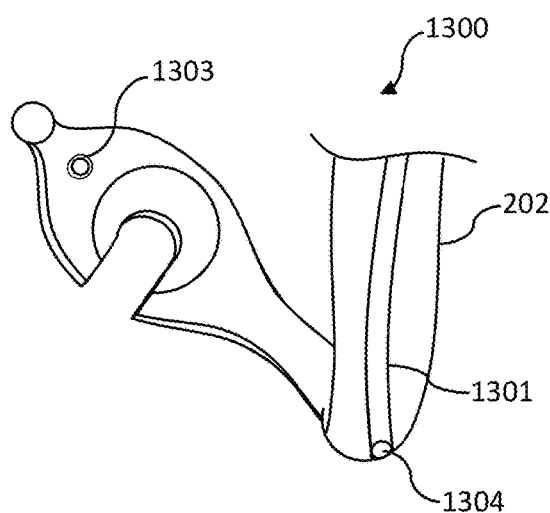

FIG. 13A shows guide body 1300 having a orientation aperture 1303 formed in reference plate 201 such that slot 1201 is interposed between orientation aperture 1303 and a orientation aperture 1304 (shown in FIG. 13C-13D). Orientation aperture 1303 may have a diameter ranging approximating 0.15 mm to 1 mm and is designed for a suture shuttle to be passable therethrough. A retaining groove 1302 is formed in handle 208 having a width operable to provide an interference fit between a shuttle suture and retaining groove 1302 for providing the necessary friction for retaining a portion of shuttle cable 1202 and may vary in width proportional to the chosen cable diameter. A retaining channel 1301 is formed on the perimeter of connecting arm 202 having a depth and width operable to contain a portion of shuttle cable 1202 below the surface of connecting arm 202 to prevent entanglement with tissue during instrument placement. FIG. 13B is a detail view of the proximal section of guide body 1300 where retaining groove 1302 and retaining channel 1301 can be appreciated. FIGS. 13C-13D are perspective views of reference plate 201 and connecting arm 202 illustrating orientation aperture 1304 which, in this example, originates at the joint of connecting arm 202 and reference plate 201 and extends through arm 202 to intersect the origination of retaining channel 1301.

Figure 14A:
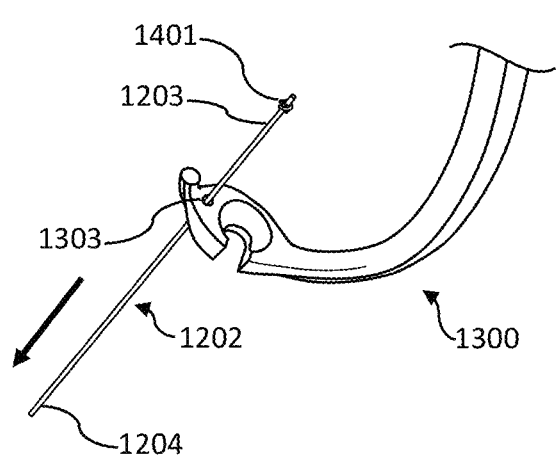
FIG. 14 illustrates exemplary steps for integrating a shuttle suture onto a drill guide body, in accordance with at least one embodiment disclosed.
Figure 14B:
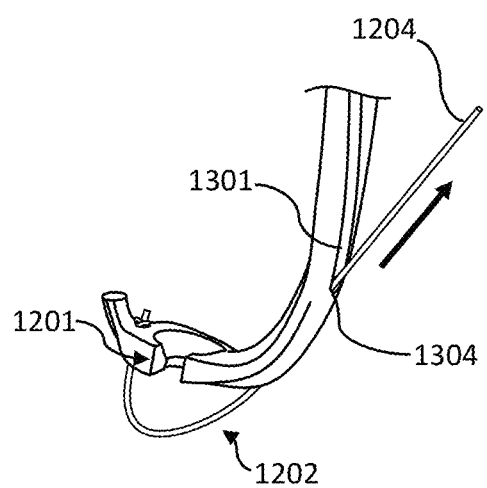
Figure 14C:
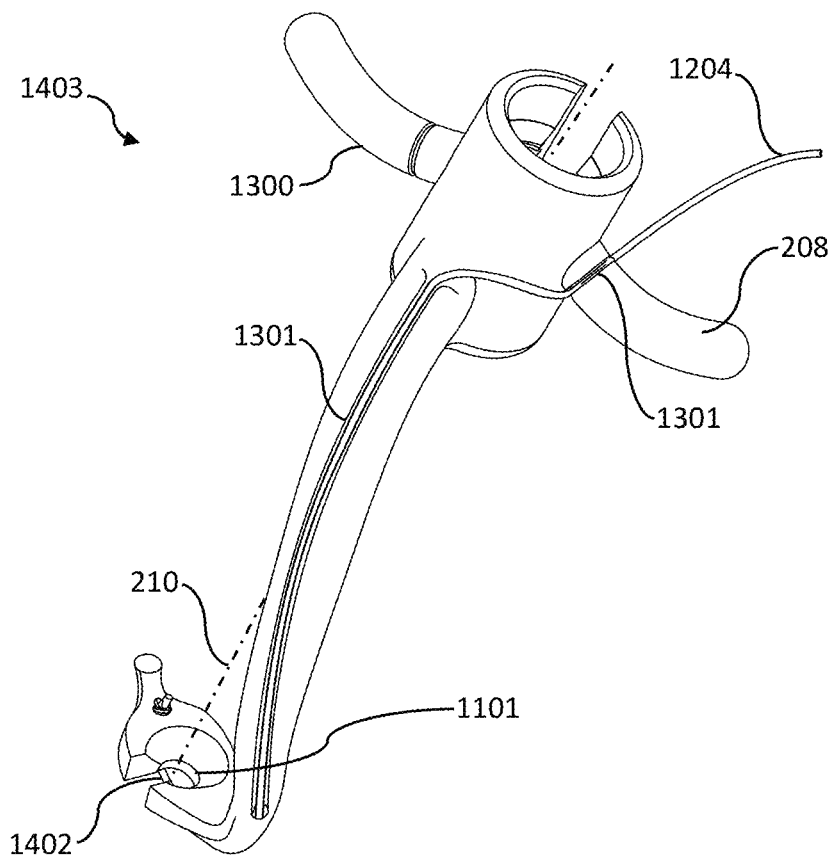

FIGS. 14A-14C illustrate exemplary steps for integrating shuttle cable 1202 onto guide body 1300 to form a shuttle assembly 1403, according to an embodiment of the present invention. As shown in FIG. 14A, a stopper knot 1401 is tied in end 1203 of shuttle cable 1202 having a diameter sufficiently large such that it will not be passable through orientation aperture 1303. End 1204 is passed through orientation aperture 1303 from the proximal side to the distal side of reference plate 201. End 1204 is then oriented to span slot 1201 and introduced into the origin of orientation aperture 1304 at the distal end of reference plate 201 to exit orientation aperture 1304 at its intersection with retaining groove 1302 as shown in FIG. 14B. FIG. 14C shows the middle portion of in shuttle cable 1202 contained in retainer channel 1301 and end 1204 secured to handle 208. In this example, end 1204 is pulled by the user into retaining groove 1302 and wrapped around the circumference of the inner diameter of retaining groove 1302 at least one time. A capture portion 1402 of shuttle cable 1202 spans aperture 1101, and is available for retrieval by instruments passed through guide aperture 1101 along guide axis 210.

Figure 15:
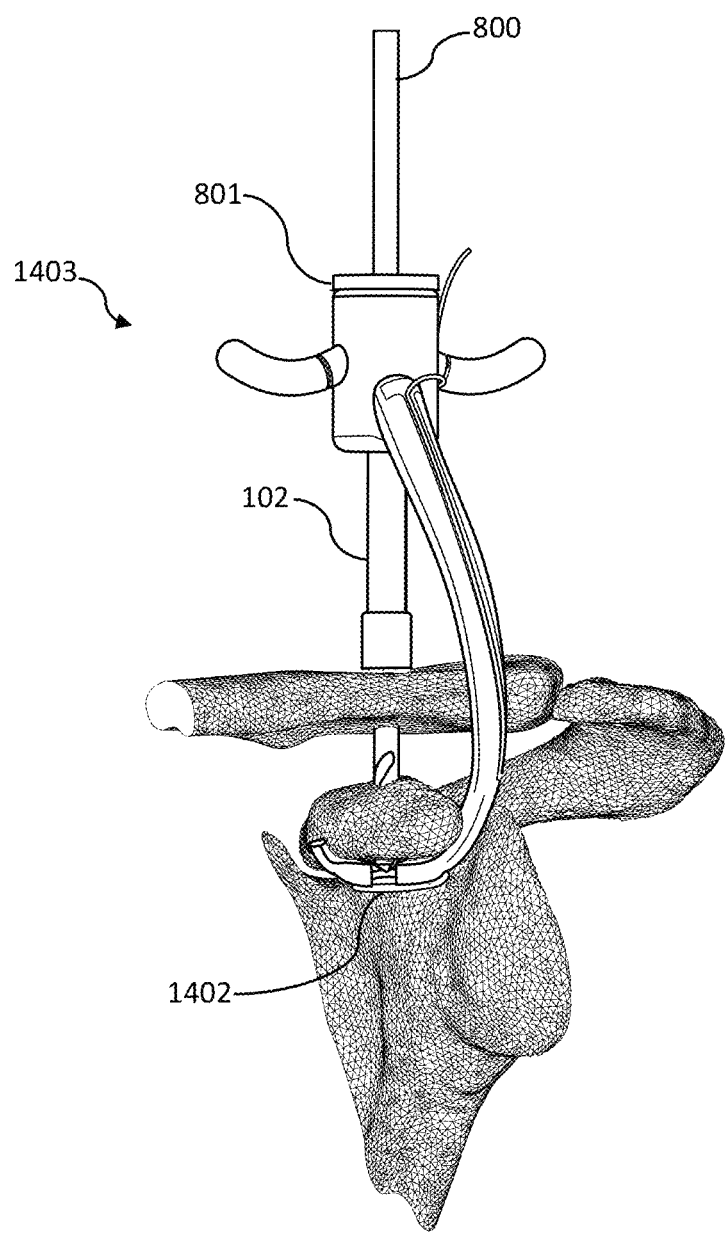
FIG. 15 illustrates perspective and close-up views, respectively, of the drill guide body of FIGS. 13A-13D integrated with a shuttle suture, in accordance with the disclosure.

FIG. 15 illustrates a perspective view of shuttle assembly 1403 during the drilling step of an acromioclavicular joint repair, in accordance with the disclosure. In this view, capture portion 1402 is provided on the distal side of reference plate 201. This design allows for depth-limited drilling through guide sleeve 102 as previously described, and prevents the cutting tip of drill 800 from contacting and possibly damaging the shuttle suture.

Figure 16B:
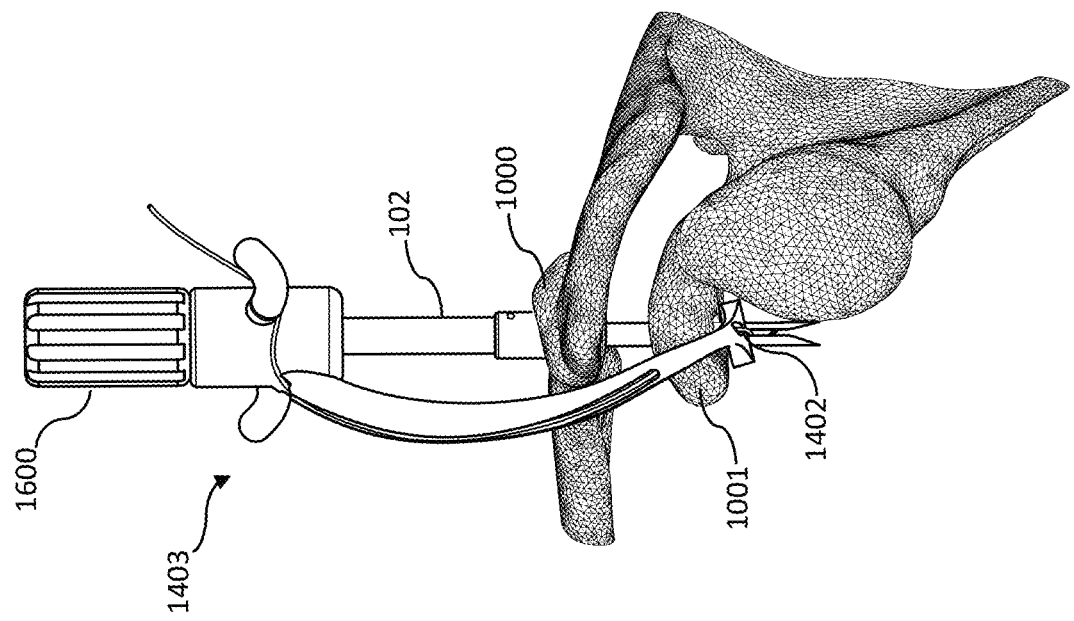
FIGS. 16A-16E illustrate exemplary use steps for placing a guide, forming an aperture, and retrieving a shuttle suture through said aperture, in accordance with at least one embodiment disclosed.
Figure 16A:
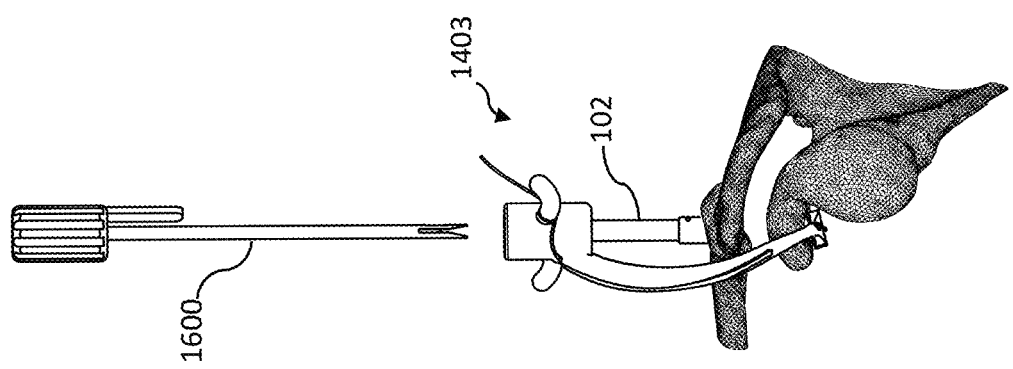
Figure 16D:
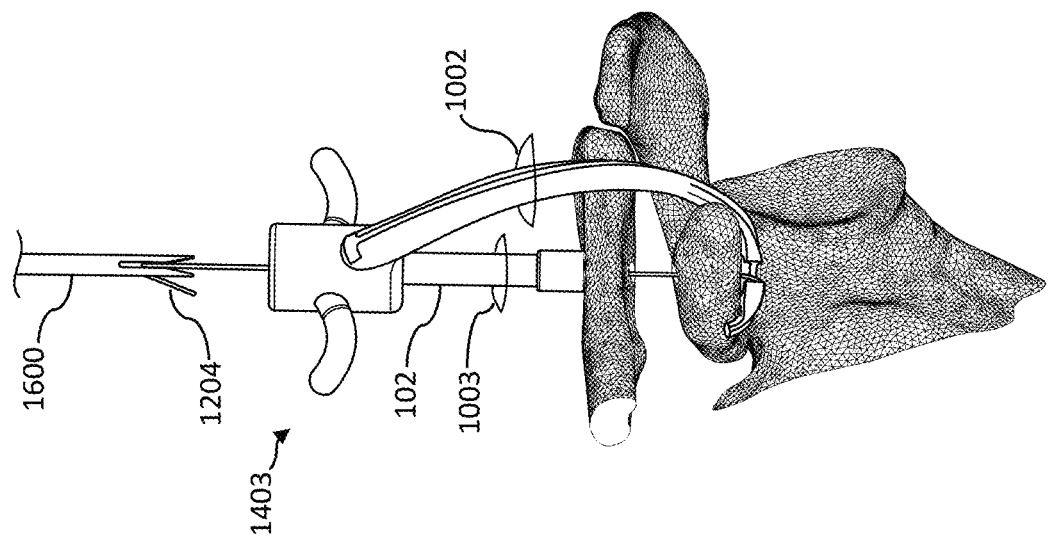
Figure 16C:
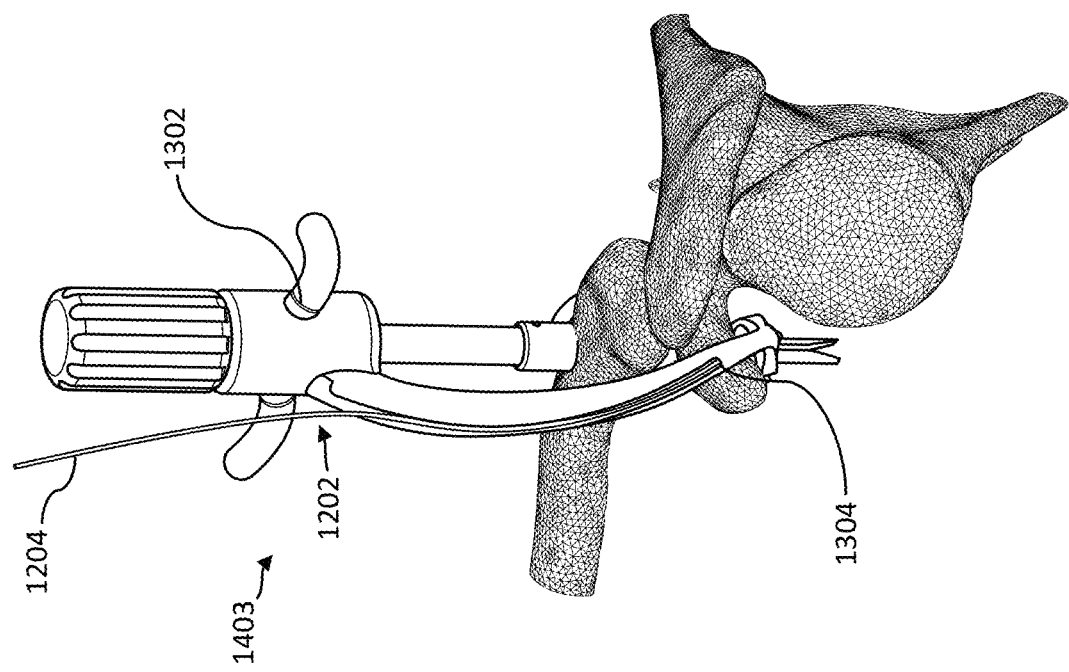
Figure 16E:
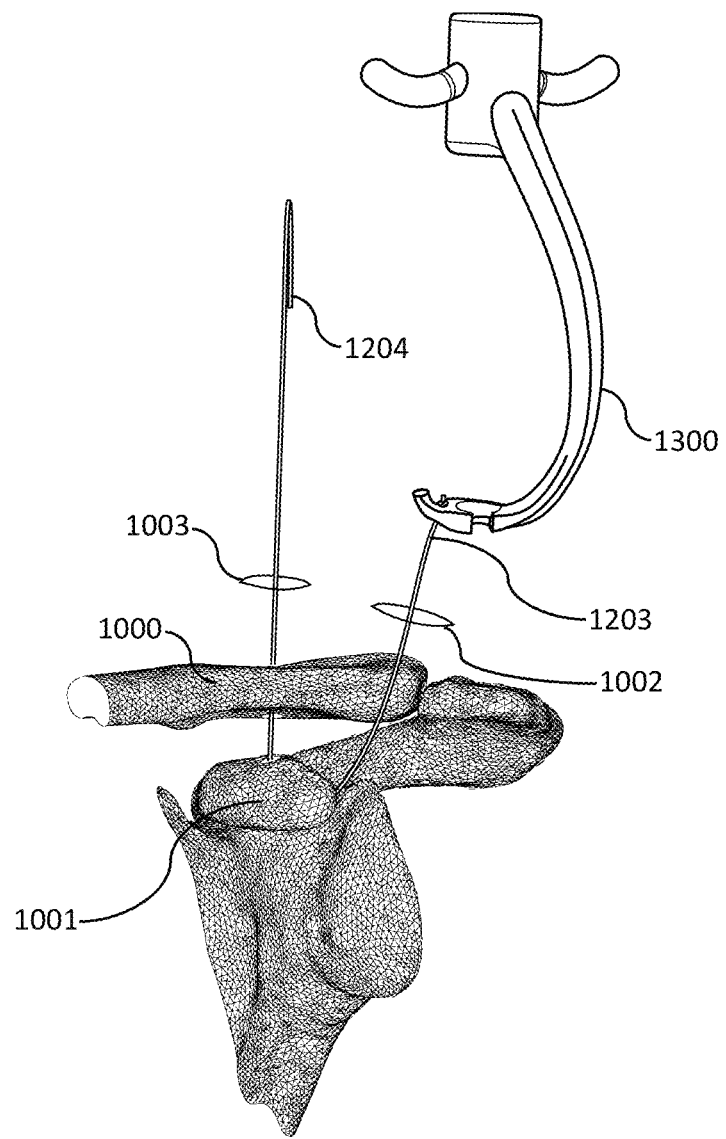

FIGS. 16A-16E illustrate exemplary use steps for transferring one end of shuttle cable 1202 from surgical portal 1002, through the apertures created in clavicle 1000 and coracoid 1001, to then exit surgical portal 1003, according to an embodiment of the present invention. FIGS. 16A-16B show a retrieval device 1600 positioned and advanced through guide sleeve 102 and the apertures drilled in clavicle 1000 and coracoid 1001 engaging capture portion 1402. End 1204 is then disengaged from retaining groove 1302 allowing free movement of shuttle cable 1202 through containment aperture 1304 during portal transfer as shown in FIG. 16C. Retrieval device 1600 is then withdrawn from guide sleeve 102 transferring end 1204 from surgical portal 1002 to surgical portal 1003 through the drilled apertures as shown in FIG. 16D. It should be noted that the coupling of retrieval device 1600 to shuttle cable 1202 should allow for shuttle cable 1202 to slide axially through the capture mechanism of retrieval device 1600 during the transfer. FIG. 16E shows guide body 1300 removed from surgical portal 1002. The connection of end 1203 to reference plate 201 causes end 1203 to be retained on the distal side of coracoid 1001 and exit surgical portal 1002 enabling a mechanical link between surgical portal 1002 and surgical portal 1003 through the apertures drilled in clavicle 1000 and coracoid 1001.

FIGS. 17A-17B illustrate side and perspective views, respectively, of a guide body 1700, according to embodiment of the present invention. In this example, guide body 1700 includes the features as described as guide body 1100 further comprising an aperture 1701 formed between the proximal and distal surfaces of reference plate 201 and intersecting guide aperture 1101, and is designed to retain shuttle cable 1202 (not shown) in a position to span guide aperture 1101 and available for engagement with a suture retrieval device introduced into guide aperture 1101.

FIGS. 17C-17D show a perspective and detail views, respectively, of a shuttle assembly 1702, according to an embodiment of the present invention, comprising shuttle cable 1202 integrated onto guide body 1700. Stopper knot 1401 is tied in end 1203 in similar fashion as described in FIG. 14 such that its diameter is sufficiently large to prevent passage through aperture 1701. End 1204 is then passed through aperture 1701 from one side of reference plate 201 exiting the opposite side such that capture portion 1402 spans guide aperture 1101 enabling engagement with a suture retrieving device introduced into guide aperture 1101. End 1204 is then passed into containment orientation aperture 1304, placed in retaining channel 1301, and secured in retaining groove 1302.

FIGS. 18A-18C illustrate exemplary steps for integrating shuttle cable 1202 onto guide body 1700 to form a shuttle assembly 1800, according to an embodiment of the present invention. As shown in FIG. 18A, end 1204 is passed through aperture 1701 from one side of reference plate 201 exiting the opposite side. End 1203 and end 1204 are then passed through orientation aperture 1304 from the bottom side of reference plate 201 as shown in FIG. 18B. The limbs of shuttle cable 1202 may then be placed in retaining channel 1301 with subsequently secured each in a separate retaining groove 1302, as shown in FIG. 18C.

Figure 19B:
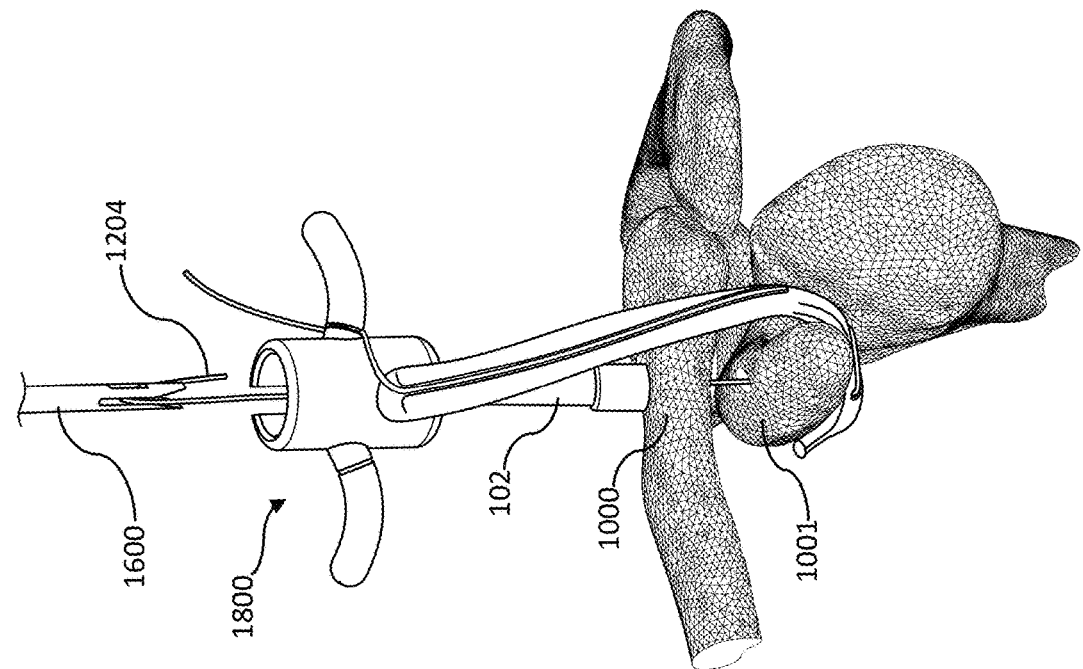
FIGS. 19A-19B illustrate perspective views of a drill guide and suture passing system, in accordance with at least one embodiment disclosed.
Figure 19A:
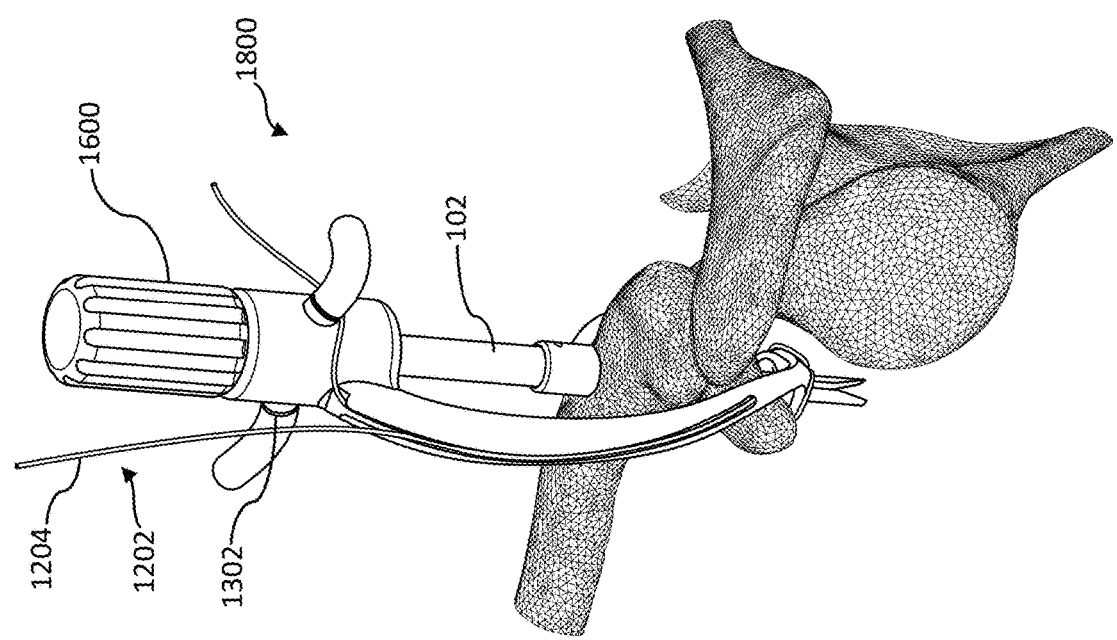
Figure 19D:
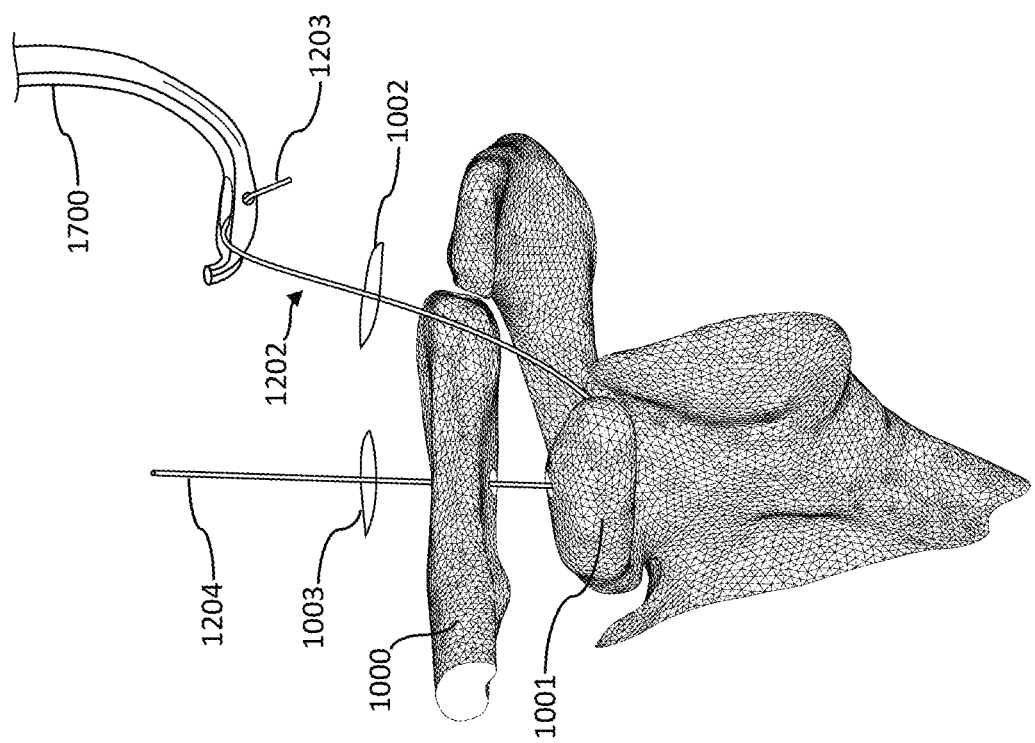
Figure 19C:
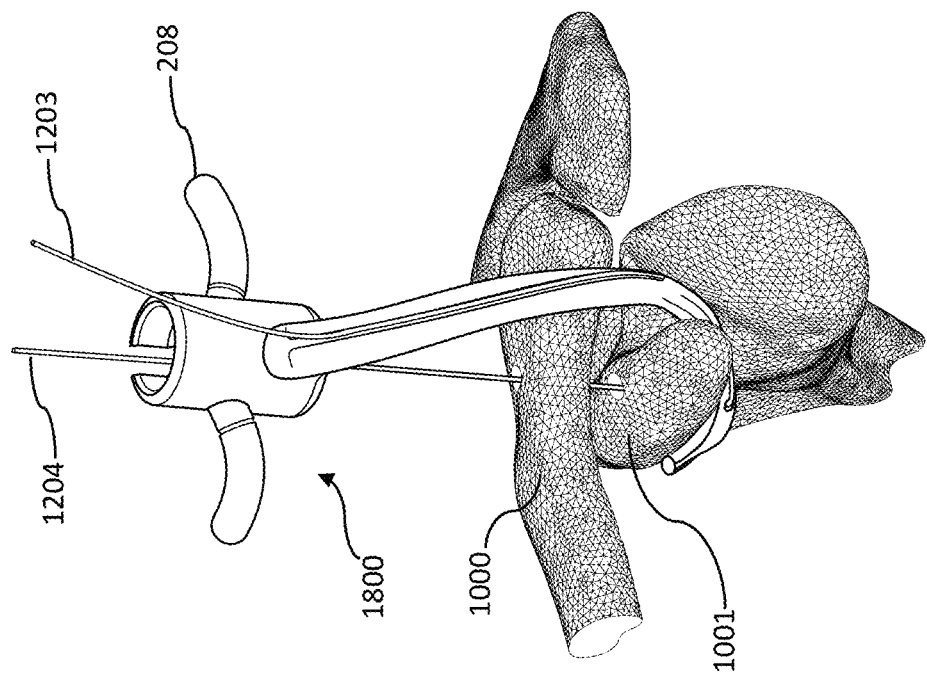

FIGS. 19A-19D illustrate exemplary steps for using shuttle assembly 1800 to transfer a limb of shuttle cable 1202 from a first side of a formed apertures in a plurality of bones to the second side, according to an embodiment of the present invention. In this example, shuttle assembly 1800 is placed interposing clavicle 1000 and coracoid 1001 and coupling guide sleeve 102 as previously described. After forming an aperture through both bones, retrieval device 1600 is then introduced into guide sleeve 102 and passed through the bone apertures to engage with capture portion 1402 as described in FIG. 16C. FIG. 19A shows end 1204 disengaged from retaining groove 1302. FIG. 19B shows retrieval device 1600 withdrawn from guide sleeve 102, thereby transferring end 1204 from the distal side of coracoid 1001 to the proximal side of clavicle 1000 through the drilled apertures. With end 1204 transferred and exiting surgical portal 1003, the user may remove guide sleeve 102 and dissociate end 1203 from handle 208 as illustrated in FIG. 19C. As shown in FIG. 19D, guide body 1700 is then removed from surgical portal 1002 with end 1204 retained on the proximal side of clavicle 1000 and exiting surgical portal 1003. It should be noted that shuttle cable 1202 now links surgical portal 1002 to surgical portal 1003 through the drilled bone apertures.

Figure 20A:
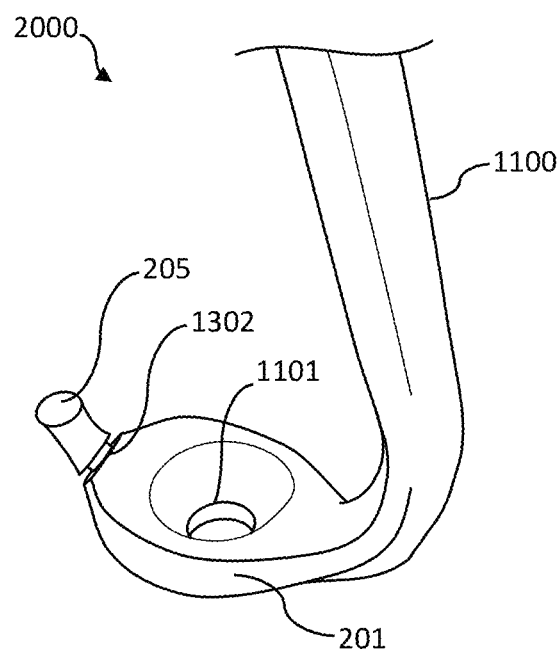
FIGS. 20A-20B illustrate close-up views of an alternative embodiment of the drill guide body of FIG. 17, in accordance with the disclosure.
Figure 20B:
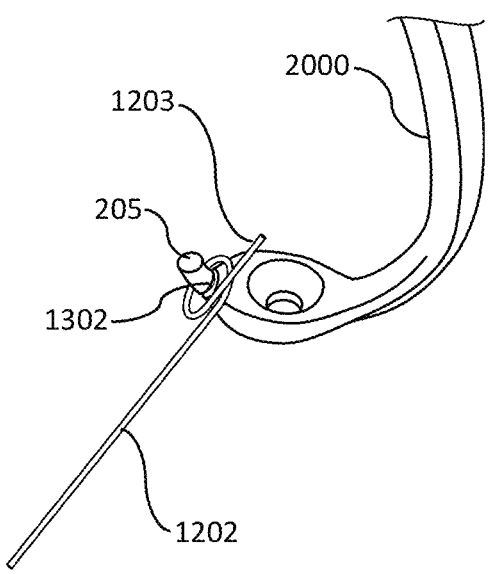
Figure 20C:
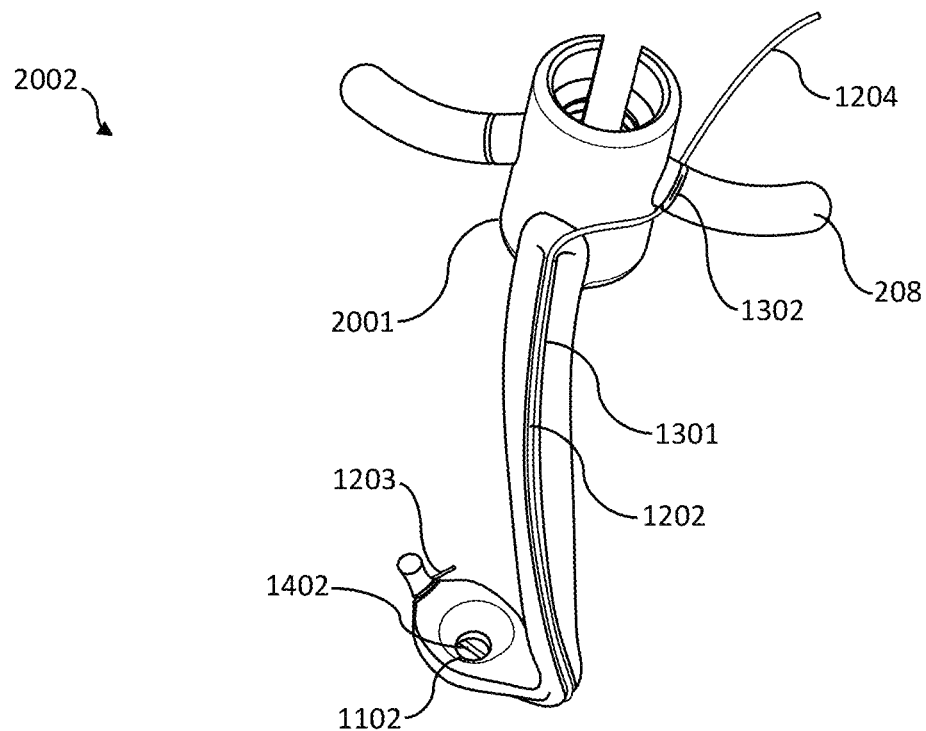

FIG. 20A shows a perspective view of the distal portion of a guide body 2000, according to another embodiment of the present invention. In this example, retaining groove 1302 is formed in probe 205. FIGS. 20B-20C illustrates shuttle cable 1202 integrated onto guide body 2000 to form a shuttle assembly 2002. In this example, end 1203 is removably secured to reference plate 201 by the engagement of end 1203 into retaining groove 1302 on probe 205. Shuttle cable 1202 may then be placed in retaining channel 1301 with end 1204 secured into retaining groove 1302 on handle 208 as previously described, with capture portion 1402 spanning guide aperture 1101 as shown.

What is claimed is:

1. A surgical guide system, comprising:
    a guide body having a receiver and a reference plate joined by a connecting arm, a portion of the receiver and a portion of the reference plate intersecting a guide axis, the receiver comprising a tubular body having a proximal end and a distal end and an adjustment aperture formed therethrough, the guide body operable for at least one bone to be interposed between the distal end of the receiver and reference plate; and
    a guide sleeve comprising a tubular body having a proximal end and a distal end and a lumen, the proximal end operable for coupling with the receiver within the adjustment aperture and adjustable therein;
    wherein the lumen of the guide sleeve is operable to guide a surgical tool along the guide axis therethrough,
    wherein the guide sleeve is recessed below the proximal end of the receiver while guiding the surgical tool,
    wherein the guide axis intersects a portion of the at least one bone interposed between the receiver and the reference plate.

2. The surgical guide system of claim 1, wherein a rotation of the guide sleeve with respect to the receiver causes a change in distance between the guide sleeve and the reference plate.

3. The surgical guide system of claim 1, the guide sleeve further includes a locating member comprising a tubular body having a proximal end and a distal end rotatable on the guide sleeve.

4. The surgical guide system of claim 3, the locating member further comprising:
    a reference arm extending from the tubular body having a portion offset from the guide axis;
    wherein a portion of the reference arm is operable to contact a portion of a first surface on the at least one bone interposed between the receiver and the reference plate, the guide axis intersecting a second surface on the at least one bone, the second surface not parallel to the first surface,
    wherein the reference arm limits the distance between the first surface and the guide axis.

5. The surgical guide system of claim 4, the locating member further comprising at least one gripping feature extending from the distal end of the tubular body, wherein the gripping feature is operable to improve traction between the locating member and the at least one bone.

6. The surgical guide system of claim 1, the receiver further comprising a slot, wherein the slot is parallel to the guide axis.

7. The surgical guide system of claim 1, the receiver further comprising a scale, wherein the scale is calibrated to provide a measurement of the distance between the guide sleeve and the reference plate when a designated feature of the of the drill sleeve and the scale are both in view.

8. The surgical guide system of claim 1, further comprising a shuttle cable, wherein a first portion of the shuttle cable is coupled to the reference plate and at least a second portion of the shuttle cable is coupled in communication with the receiver, wherein a third portion of the shuttle cable is capable of being engaged with the surgical tool.

9. The surgical guide system of claim 8, wherein a portion of the shuttle cable is capable of being coupled with the connecting arm while guiding the surgical tool.

10. The surgical guide system of claim 1, the reference plate further comprising at least one orientation aperture, the orientation aperture operable for containing the shuttle cable therethrough, wherein the at least one orientation aperture positions a portion of the shuttle cable for engagement with a surgical device.

11. The surgical guide system of claim 1, the guide body further comprising at least one retainer groove, wherein the groove is operable to secure a portion of the shuttle cable.

12. The surgical guide system of claim 1, the reference plate further comprising an aperture, wherein the guide axis intersects a portion of the aperture, wherein the aperture is operable to receive a surgical instrument.

13. The surgical guide system of claim 1, the reference plate further comprising a slot formed from the proximal surface to the distal surface of the reference plate, wherein the guide axis intersects a portion of the slot.

14. The surgical guide system of claim 1 further comprising a driver, the driver comprising a driver body having a proximal end and a distal end and operable to couple with the guide sleeve, wherein a torque applied to the driver causes the guide sleeve to rotate.

15. The surgical guide system of claim 14, the driver body further comprising a lumen.

16. The surgical guide system of claim 15, the driver body further comprising a slot extending from the lumen through the wall of the driver body, wherein the slot is operable for the surgical tool to access the lumen through the side of the driver body.

17. The surgical guide system of claim 14, the driver further comprising a driver scale calibrated to provide a measurement of the distance between the guide sleeve and the reference plate when a designated feature of the of the guide body and the driver scale are both in view.

18. A method of transporting a shuttle cable through at least one bone comprising the steps:
    positioning the surgical guide system of claim 8 on at the least one bone, the at least one bone having a first side and a second side, wherein the at least one bone is interposed between the receiver and the reference plate, the guide sleeve contacting the first side of the at least one bone and the reference plate contacting the second side of the at least one bone, wherein the guide axis intersects a bone hole formed in the at least one bone, the bone hole having a first hole end and a second hole end;
    passing the surgical tool through the bone hole in the at least one bone from the first hole end to the second hole end;
    engaging the surgical tool with the third portion of the shuttle cable; retrieving the second portion of the shuttle cable through the bone hole from the second hole end to the exit the first hole end; and
    moving the guide body away from the at least one bone;
    wherein moving the guide body away from the at least one bone the second portion causes the first portion of the shuttle cable to be available for manipulation from the second hole end.

19. The method of claim 18, further comprising the step of forming the bone hole in at least one bone from a first side to a second side, wherein the bone hole is colinear with the guide axis.

* * * * *